(12) United States Patent
Aggarwal et al.

(10) Patent No.: US 9,147,040 B2
(45) Date of Patent: Sep. 29, 2015

(54) POINT-IN-TIME QUERY SYSTEM

(71) Applicant: Oracle International Corporation, Redwood Shores, CA (US)

(72) Inventors: Amit Aggarwal, Irvine, CA (US); William Andrew Triebel, San Francisco, CA (US); Puneet Singhal, Ghaziabad (IN)

(73) Assignee: Oracle International Corporation, Redwood Shores, CA (US)

( * ) Notice: Subject to any disclaimer, the term of this patent is extended or adjusted under 35 U.S.C. 154(b) by 225 days.

(21) Appl. No.: 13/923,483

(22) Filed: Jun. 21, 2013

(65) Prior Publication Data

US 2014/0122523 A1    May 1, 2014

Related U.S. Application Data

(60) Provisional application No. 61/720,611, filed on Oct. 31, 2012.

(51) Int. Cl.
*G06F 17/30* (2006.01)
*G06F 19/00* (2011.01)
*G06Q 50/24* (2012.01)

(52) U.S. Cl.
CPC ........ *G06F 19/322* (2013.01); *G06F 17/30424* (2013.01); *G06F 17/30525* (2013.01); *G06F 19/3443* (2013.01); *G06F 19/36* (2013.01); *G06Q 50/24* (2013.01); *G06F 19/363* (2013.01)

(58) Field of Classification Search
CPC ........................ G06F 17/30424; G06F 19/3443
See application file for complete search history.

(56) References Cited

U.S. PATENT DOCUMENTS

| | | | |
|---|---|---|---|
| 7,475,066 B2 | 1/2009 | Dettinger et al. | |
| 2004/0267706 A1* | 12/2004 | Springer et al. | 707/3 |
| 2007/0271242 A1* | 11/2007 | Lindblad | 707/3 |
| 2009/0055421 A1 | 2/2009 | Lier | |
| 2009/0076845 A1 | 3/2009 | Bellini et al. | |
| 2012/0089481 A1* | 4/2012 | Iozzia et al. | 705/26.41 |
| 2013/0073589 A1* | 3/2013 | Smith et al. | 707/770 |
| 2013/0212068 A1* | 8/2013 | Talius et al. | 707/639 |

OTHER PUBLICATIONS

Oracle. (Jul. 2011). Oracle Argus Safety, User's Guide, Release 6.0.1, E15952-03. [PDF file]. pp. 1 to 13-8. Available through https://docs.oracle.com/cd/E20696_01 1doc.601/e15952.pdf [Accessed Dec. 10, 2014].

Richard L. Bradshaw et al., "Architecture of a federated query engine for heterogeneous resources", AMIA 2009 Symposium Proceedings, pp. 70-74, XP055093866, http://www.pubmedcentral.nih.gov/articlerender.fcgi?artid=2815441&tool=pmcentrez&rendertype=abstract, last downloaded Dec. 17, 2013.

(Continued)

*Primary Examiner* — Mohammad S Rostami
(74) *Attorney, Agent, or Firm* — Miles & Stockbridge P.C.

(57) ABSTRACT

A system is provided that implements a point-in-time query. The system selects a point-in-time query type from one or more point-in-time query types. The system further retrieves metadata that includes structured query language information based on the selected point-in-time query type. The system further creates a point-in-time query for a data source based on the retrieved metadata, where the point-in-time query is a query that is based on a date and/or time. The system further compiles the point-in-time query. The system further executes the point-in-time query on the data source; where the executing of the point-in-time query creates a case series.

20 Claims, 16 Drawing Sheets

(56) References Cited

OTHER PUBLICATIONS

Oracle Health Sciences Cohort Explorer Release Content Document, Release 1.0, http://docs.oracle.com/cd/E24441_01/doc.10/e25021/toc.htm, Mar. 15, 2013.

Oracle Health Sciences, Oracle Data Sheet, "Oracle Health Sciences Cohort Explorer", http://www.oracle.com/us/industries/health-sciences/hs-cohort-explorer-ds-1672120.pdf, Mar. 15, 2013.

Spotfire TIBCO Software, "TIBCO Spotfire Analylics Platform", http://spotfire.tibco.com/-/media/content-center/datasheets/spotfire-platform-overview.ashx, Mar. 15, 2013.

Oracle Health Sciences, Oracle Data Sheet, "Supporting Drug Safety and Regulatory Compliance With Oracle's Argus Safety", http://www.oracle.com/us/industries/029415.pdf, Mar. 15, 2013.

IBM Cognos Software, http://www-01.ibm.com/software/analytics/cognos/, Mar. 15, 2013.

IBM Analysis, "The full spectrum of analysis available from IBM", http://www-01.ibm.com/software/analytics/rte/an/analysis/index.html, Mar. 15, 2013.

Oracle Health Sciences, Oracle Data Sheet, "Oracle Health Sciences Clinical Development Center", http://www.oracle.com/us/industries/healthcare/healthcare-cdc-ds-349818.pdf, Mar. 15, 2013.

William Andrew Triebel et al., U.S. Appl. No. 13/790,252, filed Mar. 8, 2013.

William Andrew Triebel et al., U.S. Appl. No. 13/790,379, filed Mar. 8, 2013.

* cited by examiner

POINT-IN-TIME QUERY SYSTEM

CROSS-REFERENCE TO RELATED APPLICATIONS

This application claims priority of U.S. Provisional Patent Application Ser. No. 61/720,611, filed on Oct. 31, 2012, the subject matter of which is hereby incorporated by reference.

FIELD

One embodiment is directed to a computer system, and more particularly, to a computer system that manages clinical data.

BACKGROUND

In the domain of health sciences, such as drug safety, a "case series" is a list of adverse event cases. An "adverse event case" or "case" is a data record of a particular incident of an adverse event occurring in a patient. Each adverse event case can have a unique identifier. In health science in general, a case series can also be identified as a "patient list," or "subject list."

Many drug safety systems can produce and consume case series, where a "drug safety system" is a system that stores drug safety data, and where drug safety data includes data related to the safety of one or more drugs, such as one or more adverse event cases. Typically, inside these systems, an executable process produces a case series and passes it to one or more executable processes which operate on it. In a common scenario, an executable process that executes a query on a data source, such as a drug safety system, can produce a case series and pass it to an executable process that executes a report. In this scenario, the case series is the result of the executable process that executes the query on the data source. In other words, a list of cases that comprise the case series is a list of cases that matches the conditions specified in the query that is executed by the executable process on the data source. The report can be the desired output format of the case series, and the report can be executed by an executable process. The case series can typically contain at least the unique identifier (typically identified as a "case identifier") for each case, and may also contain additional case data or metadata that represent the adverse event cases in the case series. The data fields in the case series do not necessarily have to be the same as the data fields specified in the query or in the report. The data fields in the case series can typically be fixed while the report data fields can be changed depending on the desired output format.

Further, it can be required by the relevant industry to have a mechanism where a user can retrieve one or more case series using a point-in-time query. A "point-in-time query" is a query that is executed against data stored within a data source, based on a specified period of time (such as a date and/or time). For example, a data source, such as a drug safety system, can contain multiple revisions of data, such as a case that is a part of a case series, where different revisions are associated with its own specified period of time. A point-in-time query can be executed on the data source (e.g., a drug safety system), where the point-in-time query can return revisions of data (e.g., one or more cases that are part of a case series), that were stored in the data source as of a specified date (e.g., one month prior to the current date). Thus, the point-in-time query can return revisions of one or more cases as of the specified date. A point-in-time query generally requires more resources than a "standard" (i.e., current time) query, and thus, is generally significantly slower than a standard query. Thus, known drug safety systems typically will not provide support for point-in-time queries, or will only embed logic for a specific point-in-time query algorithm into one or more "canned" reports or data views. Such drug safety systems do not provide a flexible solution that supports different kinds of point-in-time query algorithms, and do not provide results based on different analysis needs.

SUMMARY

One embodiment is a point-in-time query system. The point-in-time query system selects a point-in-time query type from one or more point-in-time query types. The point-in-time query system further retrieves metadata that includes structured query language information based on the selected point-in-time query type. The point-in-time query system further creates a point-in-time query for a data source based on the retrieved metadata, where the point-in-time query is a query that is based on a date and/or time. The point-in-time query system further compiles the point-in-time query. The point-in-time query system further executes the point-in-time query on the data source, where the executing of the point-in-time query creates a case series.

BRIEF DESCRIPTION OF THE DRAWINGS

Further embodiments, details, advantages, and modifications will become apparent from the following detailed description of the preferred embodiments, which is to be taken in conjunction with the accompanying drawings.

DETAILED DESCRIPTION

In one embodiment, a point-in-time query system is provided that can provide an extensible framework that supports multiple point-in-time query types, where each point-in-time query type can utilize a different point-in-time query algorithm. The extensible framework can allow a user to select a point-in-time query type from a set of system-defined point-in-time query types using a user interface. The user can then provide one or more attributes to the point-in-time query system using the user interface, and the point-in-time query system can create a point-in-time query based on the point-in-time query type selected by the user, and also based on the one or more attributes provided by the user, by retrieving metadata that describes both a data source and a structured query language ("SQL"). The point-in-time query system can then execute the point-in-time query on the data source. The data source can include one or more adverse event cases, where each adverse event case includes a data record that represents an adverse event. In an alternate implementation, the data source can include one or more medical records, where each medical record is a data record that includes medical data.

Alternatively, the user can create and store SQL, and can create and store a point-in-time query type that utilizes the user-defined SQL using the user interface. In other words, the user can create a user-defined point-in-time query type that can utilize a user-defined point-in-time query algorithm. The user can then create a point-in-time query based on the user-defined point-in-time query type using the user interface. The point-in-time query system can then execute the user-defined point-in-time query on the data source.

By executing either a system-defined point-in-time query or a user-defined point-in-time query, the point-in-time query system can generate one or more case series from one or more executed point-in-time queries and can store the one or more case series in a case series repository. A "case series" is a set of one or more adverse event cases. A "patient list" is a set of one or more medical records. The point-in-time system can be used with any data model that has a SQL interface, and can be integrated with one or more software applications. As described in this specification, a "computer application," "software application," or "application" is any collection of computer programs and/or modules. For example, the point-in-time query system can be used with any human health science data model. The point-in-time query system can also be used in other domains that use a similar data model. For example, in other embodiments, the point-in-time query can be used with multiple data sources that are available to an end user, where the multiple data sources can include a combination of adverse event databases and medical history databases.

Figure 1:
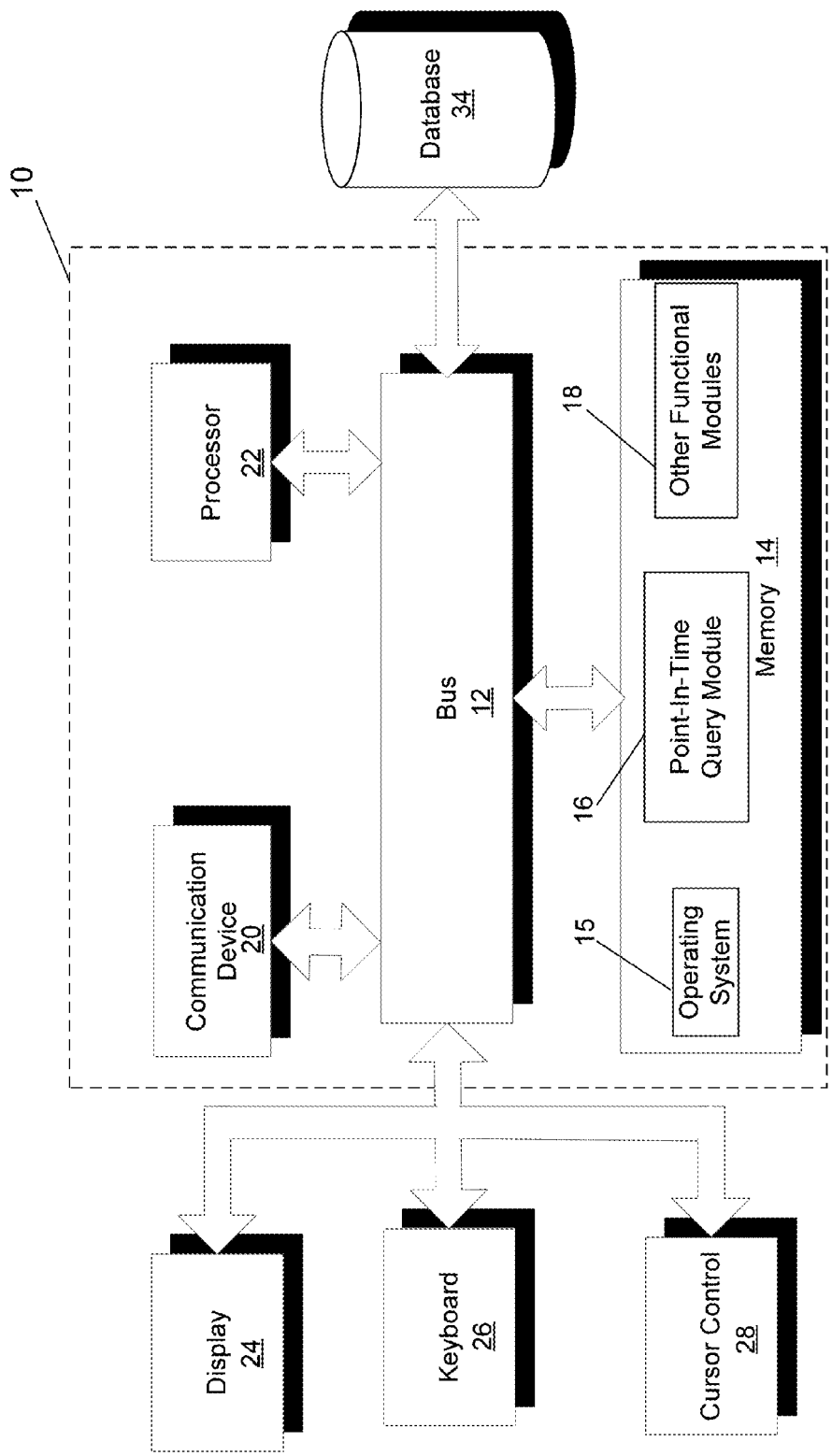
FIG. 1 illustrates a block diagram of a system that can implement an embodiment of the invention.

FIG. 1 illustrates a block diagram of a system 10 that can implement one embodiment of the invention. System 10 includes a bus 12 or other communications mechanism for communicating information between components of system 10. System 10 also includes a processor 22, operatively coupled to bus 12, for processing information and executing instructions or operations. Processor 22 may be any type of general or specific purpose processor. System 10 further includes a memory 14 for storing information and instructions to be executed by processor 22. Memory 14 can be comprised of any combination of random access memory ("RAM"), read only memory ("ROM"), static storage such as a magnetic or optical disk, or any other type of machine or computer-readable medium. System 10 further includes a communication device 20, such as a network interface card or other communications interface, to provide access to a network. As a result, a user may interface with system 10 directly, or remotely through a network or any other method.

A computer-readable medium may be any available medium that can be accessed by processor 22. A computer-readable medium may include both a volatile and nonvolatile medium, a removable and non-removable medium, a communication medium, and a storage medium. A communication medium may include computer readable instructions, data structures, program modules or other data in a modulated data signal such as a carrier wave or other transport mechanism, and may include any other form of information delivery medium known in the art. A storage medium may include RAM, flash memory, ROM, erasable programmable read-only memory ("EPROM"), electrically erasable programmable read-only memory ("EEPROM"), registers, hard disk, a removable disk, a compact disc read-only memory ("CD-ROM"), or any other form of storage medium known in the art.

Processor 22 can also be operatively coupled via bus 12 to a display 24, such as a Liquid Crystal Display ("LCD"). Display 24 can display information to the user. A keyboard 26 and a cursor control device 28, such as a computer mouse, can also be operatively coupled to bus 12 to enable the user to interface with system 10. In other embodiments, a user can interface with system 10 using a human interface device (not shown in FIG. 1), where a human interface device is a device configured to interact directly, and take input from, a user. Examples of a human interface device include a webcam, a fingerprint scanner, and a headset.

According to one embodiment, memory 14 can store software modules that may provide functionality when executed by processor 22. The modules can include an operating system 15, a point-in-time query module 16, as well as other functional modules 18. Operating system 15 can provide an operating system functionality for system 10. Point-in-time query module 16 can provide functionality for implementing a point-in-time query. In certain embodiments, point-in-time query module 16 can comprise a plurality of modules, where each module provides specific individual functionality for implementing a point-in-time query. System 10 can also be part of a larger system. Thus, system 10 can include one or more additional functional modules 18 to include the additional functionality. For example, functional modules 18 may include modules that provide additional functionality, such as a module of the "Oracle Argus Insight" product from Oracle Corporation.

Processor 22 can also be operatively coupled via bus 12 to a database 34. Database 34 can store data in an integrated collection of logically-related records or files. Database 34 can be an operational database, an analytical database, a data warehouse, a distributed database, an end-user database, an external database, a navigational database, an in-memory database, a document-oriented database, a real-time database, a relational database, an object-oriented database, or any other database known in the art. Further, database 34 can be accessed through an API, and can support a query language.

Figure 2:
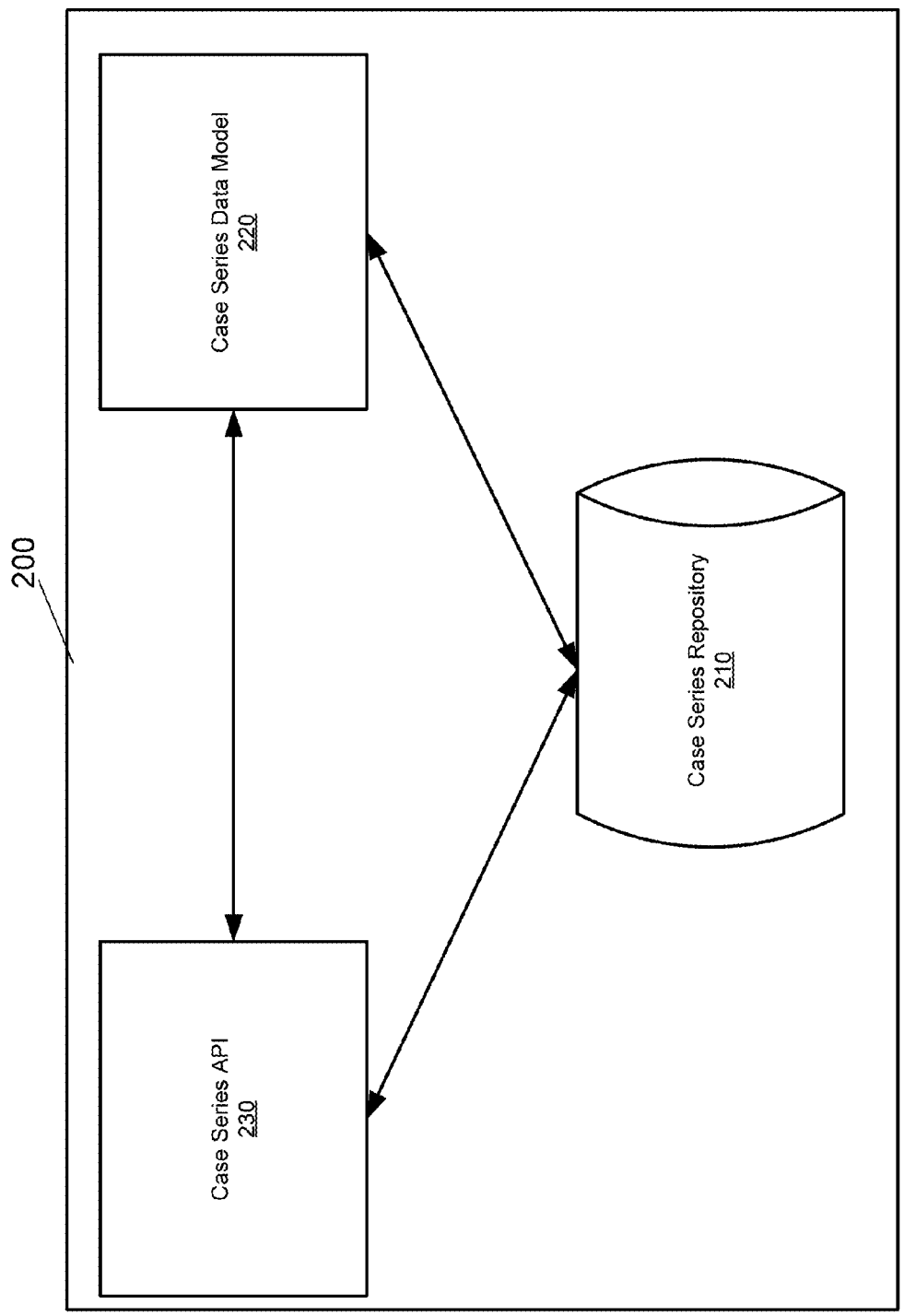
FIG. 2 illustrates a block diagram of an interoperable case series system, according to an embodiment of the invention.

FIG. 2 illustrates a block diagram of an interoperable case series system 200, according to an embodiment of the invention. Interoperable case series system 200 can include case series repository 210, case series data model 220, and case series API 230. In certain embodiments, interoperable case series system 200 can also include a user interface component (not illustrated in FIG. 2) that provides functionality for browsing and manipulating one or more case series.

According to the embodiment, case series repository 210 is a repository that can store data, such as one or more case series. For example, in an embodiment where a case series includes one or more case identifiers (where each identifier uniquely identifies each adverse event case included within the case series), and further includes case data and/or case metadata that together represent the one or more adverse event cases included within the case series, case series repository 210 can store the one or more case identifiers, and the associated case data and/or case metadata. Furthermore, for each case series, case series repository 210 can also store information related to each case series, such as case series history information and case revision information, which is further described below in greater detail. Case series repository 210 can be any type of repository that can store data, such as a database or a file.

Further, according to the embodiment, case series data model 220 is a data model that can include a canonical representation of a case series, and information related to the case series. For example, in an embodiment where a case series includes one or more case identifiers and further includes case data and/or case metadata that together represent the one or more adverse event cases included within the case series, case series data model 220 can include a data field that represents the case identifier, and one or more additional data fields that represent the case data and/or case metadata.

Furthermore, where the case series includes information related to the case series, case series data model 220 can further include one or more additional data fields that represent the information related to the case series. In certain embodiments, the information related to the case series can include case series history information. Case series history information can include information regarding the history of the case series, such as the individual that generated the case series, the mechanism that generated the case series, the one or more individuals that have modified the case series, etc. In certain embodiments, case series history information can be stored in a format of one or more change logs that can be associated with a case series.

In other embodiments, the information related to the case series can include case revision information. Case revision information can include information regarding one or more revisions of the case series. According to an embodiment, a revision is any change to an adverse event case of the case series. Thus, according to the embodiment, a case series can include one or more case revisions. Further, each case revision can be identified by the partner application that created the case revision.

In addition to, or as an alternative to including information regarding one or more revisions of the case series, case revision information can include information regarding one or more versions of the case series. According to an embodiment, a version is a change to an adverse event case of the case series that has gone through a quality analysis cycle, and is identified as ready for scientific analysis. In one example, a producing software application may include in-process revisions to cases, but a consuming software application may only support work with final versions. Case series data model 220, in conjunction with case series API 230, can allow the software applications to interpret the case revision information so that it can be most accurately used in the consuming software application. Thus, a case series can also be identified as a case revision series. Further, case revision information can include multiple revisions of the same case. In certain embodiments, case revision information can be stored in a format of one or more revisions that can be associated with a case series. An example of case series data model 220 is further described in relation to FIG. 3.

According to the embodiment, case series API 230 is an API that can expose case series data model 220, and that can represent case series data model 220 to a software application based on a format specified by the software application. Thus, case series API 230 can allow a software application to interface with case series repository 210. According to an embodiment, case series API 230 can provide functionality for producing, consuming, searching for and/or updating one or more case series. Further, in one embodiment, a first software application can produce a case series and store the case series in case series repository 210 using case series API 230. According to the embodiment, a second software application can consume the case series produced by the first software application and stored within case series repository 210 using case series API 230. Thus, rather than requiring the first software application to export the case series, and requiring the second software application to import the case series, the two software applications can interface with case series repository 210 using case series API 230.

According to an embodiment, case series repository 210, case series data model 220, and case series API 230 support four kinds of case series: (1) named case series; (2) active user case series; (3) single-use case series; and (4) case hit list. A named case series is a case series that includes an explicit unique name. The name can be given to the named case series by a user or by a function or executable process of a producing software application. Further, a software application can request a named case series by name. Case series repository 210 can support search or browse functions on a named case series. An active case series is a case series that is associated with a user. An active case series can be named for the user that the active case series is associated with. Content of an active case series can exist until it is overwritten. Thus, an active case series can allow for the creation of a personal work space that can span multiple software applications. A single-use case series is a case series that can exist within case series repository 210 for the single purpose of executing a single report. After a transaction completes, a single-use case series can be deleted. Case series repository 210 can orchestrate the execution of the report through an API that is separate from case series API 230. A case hit list is a case series that can be completely managed by a producing software application. When a case hit list is stored in case series repository 210, the case hit list can be given an identity known only to the producing software application. A case hit list does not appear in a list of named case series, but can be accessible to a consumer who is passed the identity by the producing software application.

Additionally, in one embodiment, case series repository 210, case series data model 220, and case series API 230 support other series that are very similar to case series: (1) event series; and (2) product series. A query for a particular adverse event that can be executed on a data source, such as a drug safety system, can produce a case series that can be stored within case series repository 210. Each case in the case series can have at least one event that matches the query. However, each case may also include additional events that do not match the query. Thus, a case series can include all cases that match a query, and all of the events related to those cases, whether the event matches the query or not. In contrast, an event series that is produced from a query executed on a data source can include all cases that match the query, but only include the events related to those cases that match the query as well. Further, a query for a particular medicinal or pharmaceutical product can also produce a case series. Each case in the case series can have at least one product that matches the query. However, each case may also include additional products that do not match the query. Thus, a case series can include all cases that match a query, and all of the products related to those cases, whether the product matches the query or not. In contrast, a product series that is produced from a query executed on a data source can include all cases that match the query, but only include the products related to those cases that match the query as well. Additionally, named event series, named product series, active event series, active product series, single-use event series, single-use product series, event hit lists and product hit lists are valid variations, and can work in an analogous way, to the named case series, active case series, single-use case series, and case hit lists, previously described above.

According to an embodiment, case series API 230 can execute the following functions on a case series, event series, or product series: (a) view a series; (b) save a series; (c) make a series active; (d) assign access rights to a series; (e) add a case to a series; (f) delete a case from a series; (g) delete a series; (h) annotate a case; (i) annotate a series; (j) export a series; (k) freeze a series; and (l) merge two series. The aforementioned functionality is further described in greater detail.

A user can view information stored in a series including one or more case identifiers, case revision information, case series history information, any other information related to the series, a query criteria that created the series, or any other properties and/or metadata of the series. Viewing can include searching and sorting functionality. A user can also save a series and give it a name, making it a named series. A user can make a series into an active series. A user who created a series can assign access rights to the series, such as read access and/or write access. Additionally, a user can add a case to a series. A user can also delete a case from a series. Further, a user can delete a series from case series repository 210. Also, a user can make a text annotation to a case in a series in the context of that series. If the same case appears in other series, the annotations for the case in the various series can be separate. A user can also make text annotations at a series level. Additionally, a user can export a series to a file. Further, a user can freeze a series, where the case data in the series does not change after the date and time it was frozen, even if the cases are updated in a corresponding data source that includes the case data, such as a drug safety system. A user can also unfreeze a series, so that the case data can again reflect the most current revisions available. A user can also merge two series using a union, intersect or minus operation, and thereby create a new series.

Case series API 230 can further provide the functionality to perform produce, consume, search, and update functions, according to the embodiment. In performing a produce function, case series API 230 can receive a series and store the series within case series repository 210. In performing a consume function, case series API 230 can retrieve a series from case series repository 210 and implement the series within a software application (such as displaying the series within a user interface of the software application). In performing a search function, case series API 230 can search for a series stored within case series repository 210. In performing an update function, case series API 230 can update a series stored within case series repository 210.

In certain embodiments, an embodiment can add new case series to case series repository 210 by executing a query on a data source, such as a drug safety system, where one or more cases returned by the query can be stored within case series repository 210 as a case series. Additionally, in some of these embodiments, a user can add new series to case series repository store in other ways than be executing a query on a data source. More specifically, a user can add a new series by: (a) entering a series; or (b) importing a series. By entering a series, a user can manually enter one or more case identifiers within case series repository 210 to create one or more new series. Alternately, a user can import a new series into case series repository 210 from a file containing one or more case identifiers.

Figure 3:
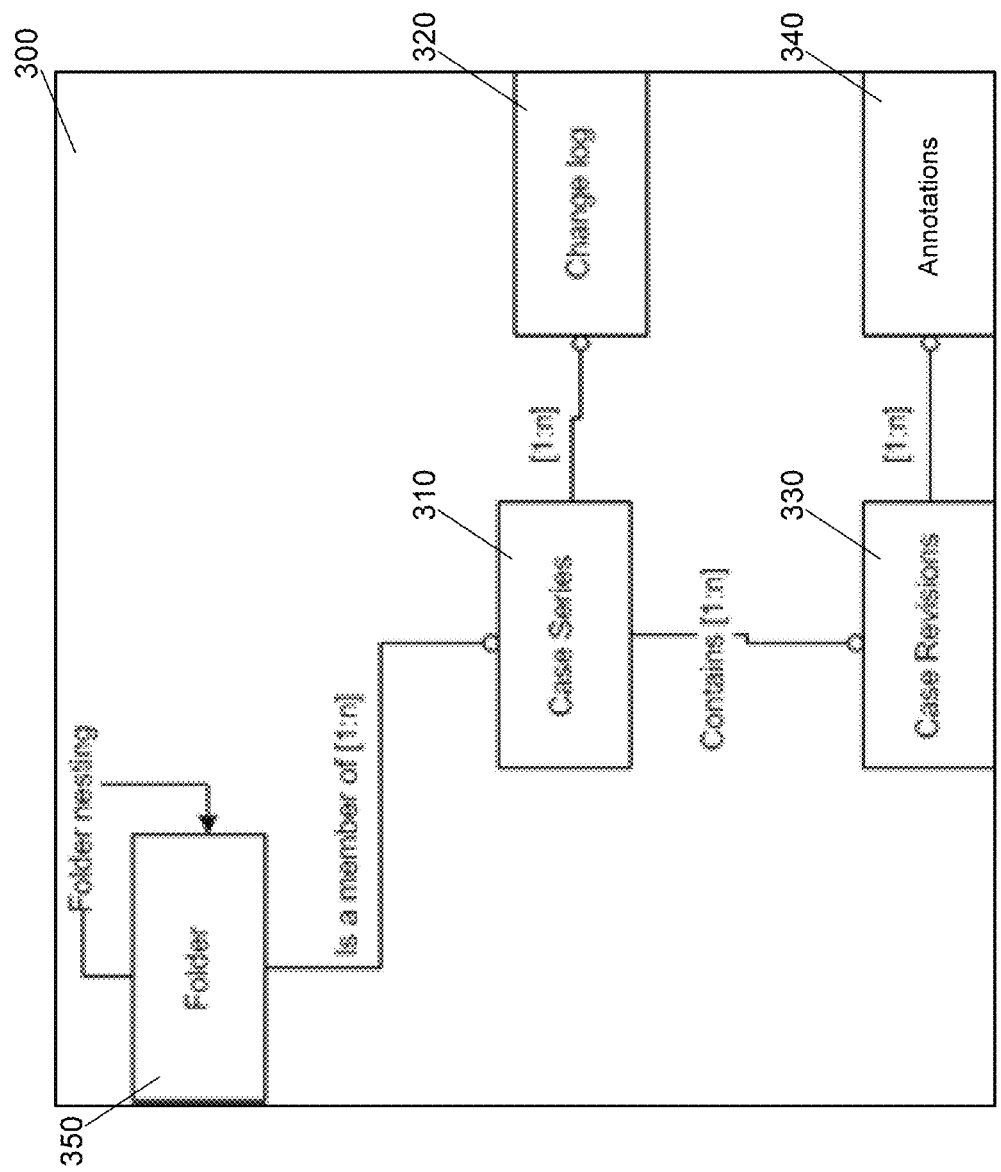
FIG. 3 illustrates a block diagram of a case series data model, according to an embodiment of the invention.

FIG. 3 illustrates a block diagram of a case series data model 300, according to an embodiment of the invention. In certain embodiments, case series data model 300 is identical to case series data model 220 of FIG. 2. As previously described, case series data model 300 includes a canonical representation of one or more case series, and information related to each case series, such as case series history information related to each case series, and case revision information related to each case series. As described below in greater detail, case series data model 300 can include a plurality of data fields, where each data field can represent a data field of a case series repository (such as case series repository 210 of FIG. 2), and where each data field can be represented in its own unique format by a case series API (such as case series API 230 of FIG. 2).

According to the embodiment, case series data model 300 includes case series 310. Case series 310 is a canonical representation of one or more case series. In certain embodiments, case series 310 includes a plurality of data fields, where each data field can store case data or metadata of each case series of the one or more case series. In some of these embodiments, case series 310 includes a data field that can store a case identifier of a case of the case series, and includes one or more data fields that can store case data or metadata that represent the one or more adverse event cases included within the case series. Thus, case series 310 can store a case identifier for each case of the case series, and case series 310 can store the data and/or metadata related to each case of the cases series. Thus, in these embodiments, case series 310 can represent one or more case series by storing a plurality of values within a plurality of data fields.

Case series data model 300 also includes change log 320. Change log 320 is a canonical representation of case series history information that is related to a case series. As previously described, case series history information can include information regarding the history of a case series, such as the individual that generated the case series, the mechanism that generated the case series, the one or more individuals that have modified the case series, etc. In certain embodiments, change log 320 includes one or more data fields, where each data field can store case series history information of each case series of the one or more case series. According to these embodiments, each data field can store a value that represents a distinct component of the case series history information. For example, a first data field of change log 320 can store a name of an individual that generated a case series, a second data field can store a name of a mechanism that generated the case series, a third data field can store a name of a first individual that modified the case series, a fourth data field can store a name of a second individual that modified the case series, etc. According to an embodiment, case series 310 and change log 320 can have a one-to-many relationship, where one or more change logs can be associated with a case series. In one embodiment, change log 320 can be implemented as a character large object ("CLOB"), where each value of change log 320 can be appended to the end of the CLOB.

Case series data model 300 also includes case revision 330. Case revision 330 is a canonical representation of case revision information that is related to one or more case series. More specifically, in certain embodiments, a case series is a container that contains one or more case revisions. In some scenarios, a case series can contain multiple case revisions of the same case. In other scenarios, a case series contains one case revision for each case of the case series. As previously described, case revision information includes information regarding one or more revisions of a case series and/or one or more versions of the case series, where a revision can be any change to an adverse event case of the case series, and a version can be a change to an adverse case of the case series that has been verified according to a defined review process. In certain embodiments, case revision 330 includes one or more data fields, where each data field can store case revision information of each case series of the one or more case series. According to these embodiments, each data field can store a value that represents a distinct component of the case revision information. In certain embodiments, a revision and/or version of a case series can be represented in a format that is identical to a format of the original case series. Thus, in these embodiments, case revision 330 includes a data field that can store a case identifier of a case of the case series, and includes one or more data fields that can store case data or metadata of the case of the case series, where the case data or metadata includes the change to the adverse event case of the case series. In other embodiments, a revision and/or version of a case series can be represented in a format that solely includes the change to the adverse event case of the case series. Thus, in these embodiments, case revision 330 includes one or more data fields that store the change to the adverse event case of the case series. According to an embodiment, case series 310 and case revision 330 can have a one-to-many relationship, where one or more case revisions can be associated with a case series. In certain embodiments, case revision 330 also includes timestamp information that can be represented by two additional data fields, a valid start date/time data field, and a valid end date/time data field. The time stamp information can represent a starting date and/or time and an ending date and/or time that the revision or version of the case series is valid. Further, a valid start date/time and a valid end date/time, are both features of source data that can enable production of a case series with case revision information. The time stamp information can, either in whole or in part, identify the revision or version of the case series.

Case series data model 300 also includes annotation 340. Annotation 340 is a canonical representation of annotation information that is related to one or more case revisions of a case series. Annotation information can include any user-defined information, where the user-defined information can serve to annotate a case revision of a case series. In certain embodiments, annotation 340 includes one or more data fields, where each data field can store a user-defined value. According to an embodiment, case revision 330 and annotation 340 can have a one-to-many relationship, where one or more annotations can be associated with a case revision.

Case series data model 300 also includes folder 350. Folder 350 is a canonical representation of a logical grouping of one or more case series. Over time, a user can generate thousands of case series using case series data model 300. A nested folder storage system can be used to organize the case series. Thus, one or more case series can be associated with a folder, and one or more folders can be nested within a folder. Thus, according to an embodiment, folder 350 and case series 310 can have a one-to-many relationship, where one or more case series can be associated with a folder. In one embodiment, folder 350 is not part of case series data model 300, but instead is a representation of a folder functionality of a document management system that is leveraged in order to organize one or more case series generated using case series data model 300 into one or more folders.

Figure 4:
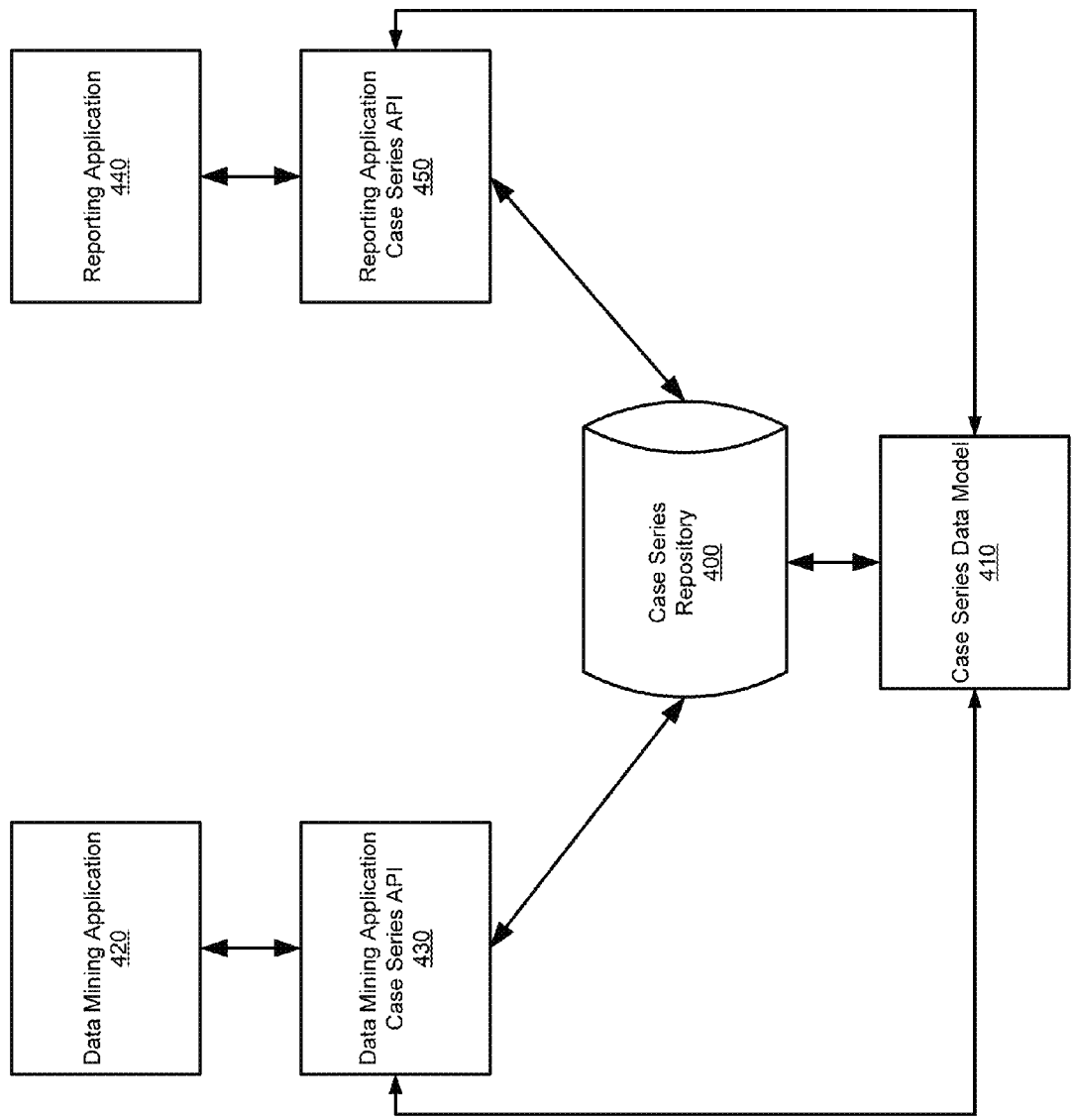
FIG. 4 illustrates a block diagram of an example implementation of an interoperable case series system, according to an embodiment of the invention.

FIG. 4 illustrates a block diagram of an example implementation of an interoperable case series system, according to an embodiment of the invention. More specifically, FIG. 4 illustrates an example of an interoperable case series system, such as interoperable case series system 200 of FIG. 2, interacting with a plurality of software applications. The implementation includes case series repository 400. As previously described, case series repository 400 is a repository that can store data, such as one or more case series, and/or information related to the one or more case series. In certain embodiments, case series repository 400 is identical to case series repository 210 of FIG. 2. The implementation further includes case series data model 410. As also previously described, case series data model 410 is a data model that can include a canonical representation of a case series, and information related to the case series. In certain embodiments, case series data model 410 is identical to case series data model 220 of FIG. 2 and case series data model 300 of FIG. 3. According to the embodiment, case series data model 410 can be a data model that represents the data stored within case series repository 400. In one embodiment, case series data model 410 can include a plurality of data fields, where the plurality of data fields represents the plurality of data fields included within case series repository 400.

The implementation further includes data mining application 420 and data mining application case series API 430. According to the embodiment, data mining application 420 is a software application that includes one or more executable processes that can execute data mining functionality to find one or more related groups of cases within drug safety data. Data mining application 420 can produce one or more case series using one or more data mining algorithms. Data mining application 420 can further consume one or more case series produced by another software application. In one embodiment, data mining application is an "Empirica Signal" product from Oracle Corporation.

Also according to the embodiment, data mining application case series API 430 provides an interface that exposes case series data model 410 to data mining application 420, that represents case series data model 410 to data mining application 420 based on a format specified by data mining application 420, and, thus, that allows data mining application 420 to interface with case series repository 400. Therefore, data mining application 420 can produce one or more case series, and can store the one or more produced case series within case series repository 400, using data mining application case series API 430. Likewise, data mining application 420 can retrieve one or more case series from within case series repository 400, and can consume the one or more retrieved case series, using data mining application case series API 430. In certain embodiments, data mining application case series API 430 represents a component of case series API 230 of FIG. 2.

The implementation further includes reporting application 440 and reporting application case series API 450. According to the embodiment, reporting application 440 is a software application that includes one or more executable processes that can execute reporting functionality to generate one or more reports that visualize one or more case series. Reporting application 440 can produce one or more case series using one or more reporting algorithms. Reporting application 440 can further consume one or more case series produced by another software application. In one embodiment, reporting application 440 is an "Oracle Argus Insight" product from Oracle Corporation.

Also according to the embodiment, reporting application case series API 450 provides an interface that exposes case series data model 410 to reporting application 440, that represents case series data model 410 to reporting application 440 based on a format specified by reporting application 440, and, thus, that allows reporting application 440 to interface with case series repository 400. Therefore, reporting application 440 can produce one or more case series, and can store the one or more produced case series within case series repository 400, using reporting application case series API 450. Likewise, reporting application 440 can retrieve one or more case series from within case series repository 400, and can consume the one or more retrieved case series, using reporting application case series API 450. Further, reporting application case series API 450 can simplify the use of case series in a report of reporting application 440, can allow a report of reporting application 440 to execute a query and use the resulting case series, and, if desired, can store the resulting case series in case series repository 400 for further use. In certain embodiments, reporting application case series API 450 represents a component of case series API 230 of FIG. 2.

Thus, according to the embodiment, data mining application 420 can interact with reporting application 440, and vice-versa, as reporting application 440 can access one or more case series produced by data mining application 420, and data mining application 420 can access one or more case series produced by reporting application 440. One of ordinary skill in the art would readily appreciate that data mining application 420 and reporting application 440 are examples of software applications that produce and consume case series according to the embodiment, and that, in alternate embodiments, data mining application 420 and reporting application 440 can be replaced with other software applications that include alternate functionality. Further, there can be any number of case series APIs that support any number of software applications, and that can allow any number of software applications to access case series repository 400 using case series data model 410.

Figure 5:
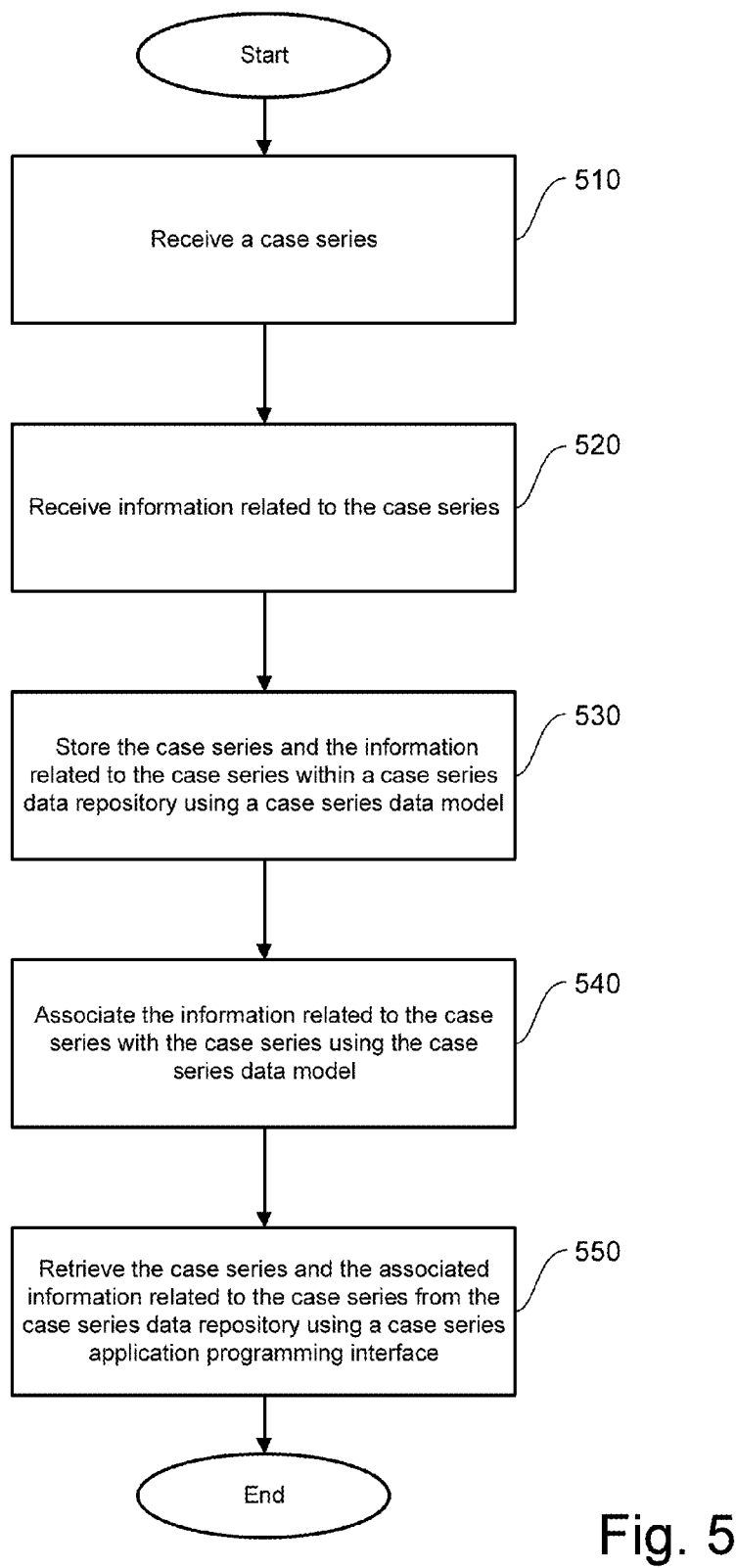
FIG. 5 illustrates a flow diagram of the functionality of an interoperable case series module, according to an embodiment of the invention.

FIG. 5 illustrates a flow diagram of the functionality of an interoperable case series module, according to an embodiment of the invention. In one embodiment, the functionality of the flow diagram of FIG. 5 (described below), as well as the functionality of the flow diagram of FIG. 8 (also described below), the functionality of the flow diagram of FIG. 11 (also described below), the functionality of the flow diagram of FIG. 12 (also described below), the functionality of the flow diagram of FIG. 13 (also described below), and the functionality of the flow diagram of FIG. 16 (also described below), are each implemented by software stored in a memory or some other computer-readable or tangible medium, and executed by a processor. In other embodiments, each functionality may be performed by hardware (e.g., through the use of an application specific integrated circuit ("ASIC"), a programmable gate array ("PGA"), a field programmable gate array ("FPGA"), etc.), or any combination of hardware and software.

The flow begins and proceeds to 510. At 510 a case series is received. In certain embodiments, the case series is received from a partner application. The case series includes one or more adverse event cases, and each adverse event case includes a data record that represents an adverse event. The case series can be a named case series, an active user case series, a single-use case series, or a case hit list. The case series can further be an event series or a product series. In certain embodiments, each data record that represents an adverse event further includes drug safety data, where drug safety data includes one or more reports or patient identifiers that are related to the safety of one or more drugs. In certain embodiments, the case series can include a plurality of case revisions. The flow proceeds to 520.

At 520, information related to the case series is received. In certain embodiments, the case series is received from a partner application. In certain embodiments, the information related to the case series includes case revision information, where case revision information can include at least one change to an adverse event case of the case series. In these embodiments, a case revision is received that includes the case revision information. In certain embodiments, where the at least one change to the adverse event case of the case series is verified according to a defined review process, a case version is received that includes the case revision information. Further, in certain embodiments, the case revision information includes timestamp information that identifies the case revision. The timestamp information can include a valid start date and/or time and a valid end date and/or time.

In other embodiments, the information related to the case series includes case series history information, where case series history information can include information regarding the history of the case series, such as an individual that generated the case series, a mechanism that generated the case series, or one or more individuals that have modified the case series. In these embodiments, a change log is created that includes the case series history information. In other embodiments, the information related to the case series includes user-defined information. In these embodiments, an annotation is created that includes the user-defined information. In other embodiments, the information related to the case series includes a logical organization of the case series and one or more additional case series. In these embodiments, a folder is created that includes the logical organization of the case series and the one or more additional case series. The flow proceeds to 530.

At 530, the case series, and the information related to the case series, are stored within a case series repository using a case series data model. A case series repository is a repository that can store data, such as one or more case series and information related to the one or more case series. A case series data model is a canonical representation of a case series that defines a format of the case series and the information related to the case series within the case series repository.

In embodiments where the information related to the case series includes case revision information, the case series data model defines a format of the case revision within the case series repository. In embodiments where the information related to the case series includes case series history information, the case series data model defines a format of the change log within the case series repository. In embodiments where the information related to the case series includes user-defined information, the case series data model defines a format of the annotation within the case series repository. In embodiments where the information related to the case series includes a logical organization of the case series and one or more additional case series, the case series data model defines a format of the folder within the case series repository.

In certain embodiments, the case series data model includes a data field that represents one or more case identifiers of the case series, and one or more additional data fields that represent the one or more adverse event cases of the case series. In these embodiments, each case identifier uniquely identifies an adverse event case of the one or more adverse event cases. Further, in some of these embodiments, the case series data model includes one or more additional fields that represent the information related to the case series.

In embodiments where the information related to the case series includes case revision information, the case series data model includes one or more additional data fields that represent the case revision information. In embodiments where the case revision information includes timestamp information, the case series data model includes one or more additional data fields that represent the timestamp information. In embodiments where the information related to the case series includes case series history information, the case series data model includes one or more additional data fields that represent the case series history information. In embodiments where the information related to the case series includes user-defined information, the case series data model includes one or more additional data fields that represent the user-defined information. In embodiments where the information related to the case series includes a logical organization of the case series and one or more additional case series, the case series data model the case series data model includes one or more additional data fields that represent the logical organization of the case series and one or more additional case series. The flow proceeds to 540.

At 540, the information related to the case series is associated within the case series using the case series data model. In embodiments where the information related to the case series includes case revision information, the case revision is associated with the case series using the case series data model. In embodiments where the information related to the case series includes case series history information, the change log is associated with the case series using the case series data model. In embodiments where the information related to the case series includes user-defined information, the annotation is associated with the case revision using the case series data model. In embodiments where the information related to the case series includes a logical organization of the case series and one or more additional case series, the case series is associated with the folder. The flow proceeds to 550.

At 550, the case series and the associated information related to the case series is retrieved from the case series repository using a case series API. The case series API is an API that that represents the case series data model to a software application based on a format specified by the software application. Thus, the case series API can define a format of the case series and the information related to the case series for the software application. The case series API can use the case series data model to retrieve the case series and the associated information form the case series repository. The flow then ends.

Figure 6:
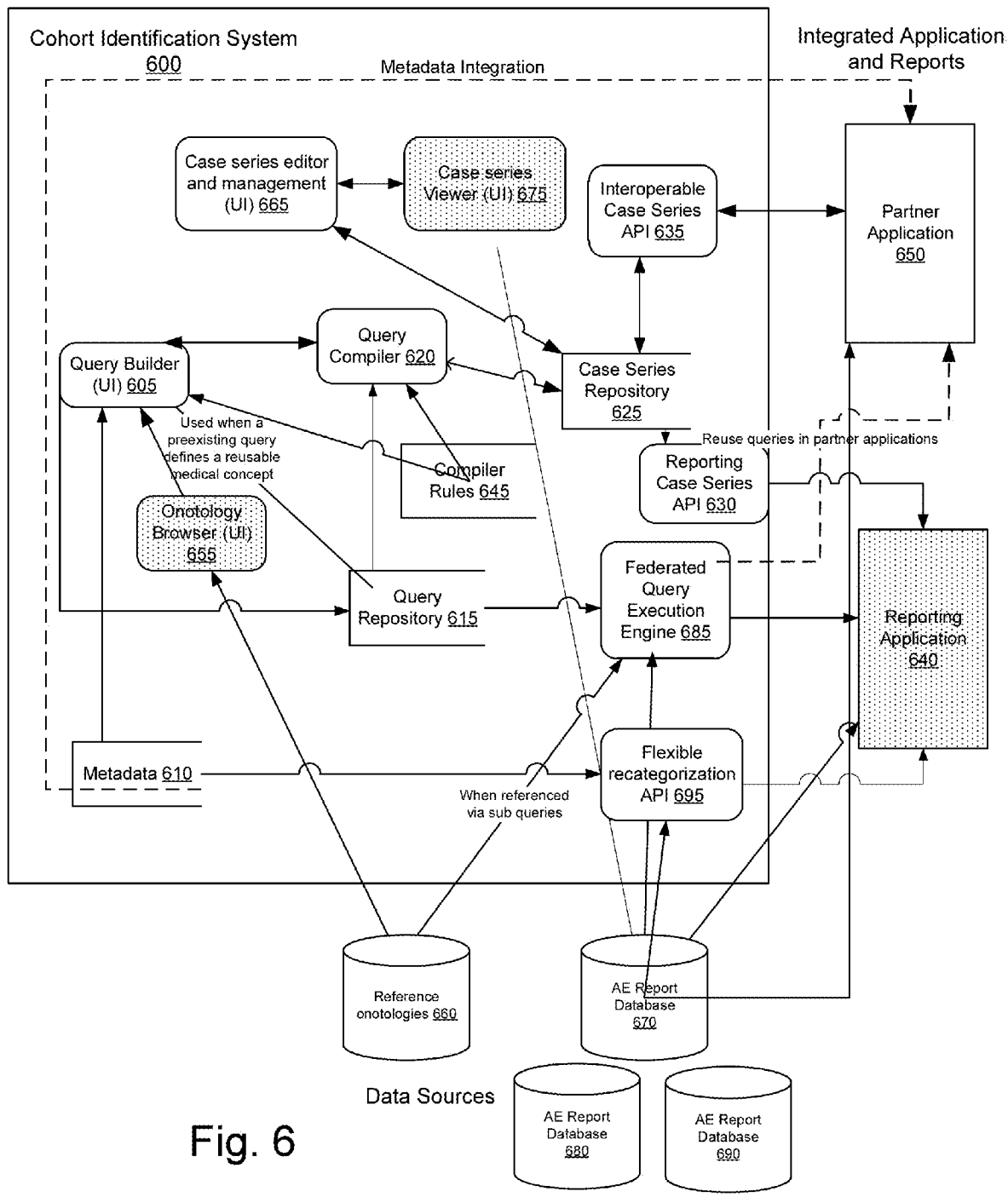
FIG. 6 illustrates a block diagram of a cohort identification system, according to an embodiment of the invention.

FIG. 6 illustrates a block diagram of a cohort identification system 600, according to an embodiment of the invention. Components of cohort identification system 600 that are shaded in FIG. 6 are components that can change depending on a data model of a data source, as will be described below in greater detail. Cohort identification system 600 can include query builder user interface ("UI") 605. Query builder UI 605 is a user interface that can be displayed to a user of cohort identification system 600, where query builder UI 605 can allow a user to create a query. In other embodiments, query builder UI 605 can display one or more data fields of a data source, and a user can select at least one of the one or more data fields to be part of the query. In these embodiments, a user can also enter criteria that can be part of the query. As will be described in greater detail, the query created by the user can be executed on a data source, such as a drug safety system, in order to retrieve data stored within the data source, such as drug safety data. In certain embodiments, a user can enter SQL syntax for the query within query builder UI 605. Further, in certain embodiments, query builder UI 605 can allow an author of the query to specify one or more place holders, identified as parameters. When the query is executed, a user can be prompted to enter a parameter value for each parameter. In addition, query builder UI 605 can also allow a user to execute a query.

Cohort identification system 600 can also include metadata 610. According to the embodiment, metadata 610 describes the data within a data source, such as drug safety data within a drug safety system. More specifically, metadata 610 describes information about each data field of the data source that can be queried. Such information can include a data type of the data field and information required to construct a structured query language ("SQL") query that include the data field. Metadata 610 can also include one or more query fields that can be derived from source data, or a combination of source data and reference data. According to the embodiment, query builder UI 605 can retrieve metadata 610 so that a user can create a query based on metadata 610 using query builder UI 605. Because of metadata 610, cohort identification system 600 is not limited to only be operatively coupled to a particular data source, or a particular data model of a data source. Instead, cohort identification system 600 is data model-independent, and can be operatively coupled with a wide variety of data sources, as will be described in greater detail. Metadata 610 can be stored in any data structure contained within cohort identification system 600, such as a repository.

Cohort identification system 600 can further include query repository 615. Query repository 615 is a repository that can store one or more queries. According to the embodiment, query builder UI 605 can store a query that is created within query builder UI 605 within query repository 615. A query created within query builder UI 605 can be stored within query repository 615 when it is determined that the query can likely be subsequently reused, such as when the query can retrieve data that will likely be used in a wide range of scenarios.

Cohort identification system 600 can also include query compiler 620. Query compiler 620 can retrieve a query that is stored within query repository 615, and can compile the stored query. By compiling the stored query, query compiler 620 can convert the query into an executable format, so that the stored query can be compiled. In some embodiments, query compiler 620 can further execute the query, once the query has been converted into an executable format. In executing the query, query compiler 620 can execute the query on a data source, and can retrieve and store data that is returned by the data source based on the query. In some embodiments, the data that is returned by the data sources includes drug safety data, where the drug safety data includes one or more adverse event cases, where each adverse event case is a data record that represents an adverse event. Further, the execution of the query can create a case series.

Cohort identification system 600 can further include case series repository 625. Case series repository 625 is a repository that can store data, such as one or more case series. For example, in an embodiment where a case series includes one or more case identifiers and further includes case data and/or case metadata that together represent the one or more adverse event cases included within the case series, case series repository 625 can store the one or more case identifiers, and the associated case data and/or case metadata. According to the embodiment, once query compiler 620 executes a query and creates a case series, query compiler can store the created case series within case series repository 625. In certain embodiments, case series repository 625 can include an associated case series data model (not illustrated in FIG. 6) that can include a canonical representation of a case series. For example, in an embodiment where a case series includes one or more case identifiers and further includes case data and/or case metadata that together represent the one or more adverse event cases included within the case series, the case series data model can include a data field that represents the case identifier, and one or more additional data fields that represent the case data and/or case metadata. In certain embodiments, case series repository 625 is identical to case series repository 210 of FIG. 2, and case series repository 400 of FIG. 4.

Cohort identification system 600 can also include reporting case series API 630. According to the embodiment, reporting case series API 630 is an API that can expose the case series data model associated with case series repository 625, and that can represent the case series data model associated with case series repository 625 to a reporting application (such as reporting application 640) based on a format specified by the reporting application. Thus, reporting case series API 630 can allow a reporting application (such as reporting application 640) to interface with case series repository 625. In other words, reporting case series API 630 can retrieve a case series from case series repository 625 and implement the series within a reporting application (such as reporting application 640). In certain embodiments, reporting case series API 630 represents a portion of case series API 230 of FIG. 2, and is identical to reporting application case series API 450 of FIG. 4. Reporting application 640 is a software application that includes one or more executable processes that can execute reporting functionality to generate one or more reports that visualize one or more case series. The generating the one or more reports can include displaying the one or more reports within reporting application 640. Reporting application 640 can also produce one or more case series using one or more reporting algorithms. Reporting application 640 can further consume one or more case series produced by cohort identification system 600 that are stored within case series repository 625 using reporting case series API 630. In certain embodiments, reporting application 640 is identical to reporting application 440 of FIG. 4.

Cohort identification system 600 can further include interoperable case series API 635. According to the embodiment, interoperable case series API 635 is an API that can expose the case series data model associated with case series repository 625, and that can represent the case series data model associated with case series repository 625 to a partner application (such as partner application 650) based on a format specified by the partner application. Thus, interoperable case series API 635 can allow a partner application (such as partner application 650) to interface with case series repository 625. In other words, interoperable case series API 635 can retrieve a case series from case series repository 625 and implement the series within a partner application (such as partner application 650). Partner application 650 is a software application that can consume one or more case series produced by cohort identification system 600 that are stored within case series repository 625 using interoperable case series API 635. Partner application 650 can also provide other functionality, such as creating one or more cases series that can be stored within case series repository 625 using interoperable case series API 635. In certain embodiments, interoperable case series API 635 is identical to case series API 230 of FIG. 2.

Cohort identification system 600 can also include compiler rules 645. According to the embodiment, compiler rules 645 can include one or more syntax rules that can be applied, by query compiler 620, to a query created by query builder UI 605 in order to determine that the query complies with the one or more syntax rules. Compiler rules 645 can be stored in any data structure contained within cohort identification system 600, such as a repository.

Cohort identification system 600 can further include ontology browser UI 655. In embodiments where a data source is a reference ontologies data source, where a reference ontologies data source is described below in greater detail, ontology browser UI 655 can retrieve one or more reference ontologies from the reference ontologies data source and display the one or more reference ontologies to a user of cohort identification system 600 within a UI. Thus, one or more elements from an ontology can be selected and used as criteria in a query.

Cohort identification system 600 can further include case series editor and management UI 665. Case series editor and management UI 665 can allow a user of cohort identification system 600 to edit and manage one or more case series stored within case series repository 625.

Cohort identification system 600 can also include case series viewer UI 675. Case series viewer UI 675 can allow a user of cohort identification system 600 to view one or more case series. The one or more case series can be stored within case series repository 625. Alternatively, the one or more case series can be stored within a data source.

Further, according to the embodiment, cohort identification system 600 can be operatively coupled to one or more data sources. As previously described, components of cohort identification system 600 (i.e., query builder UI 605 and query compiler 620) can allow a user to create and execute one or more queries on one or more data sources operatively coupled to cohort identification system 600. In certain embodiments, the one or more data sources can include drug safety data, and in some of these embodiments, drug safety data can include data related to the safety of one or more drugs, such as one or more adverse event cases. In the illustrated embodiment of FIG. 6, the one or more data sources include reference ontologies data source 660, and adverse event report databases 670, 680, and 690. Reference ontologies data source 660 is a data source that includes data regarding reference ontologies. Examples of reference ontologies data source 660 include a Systematized Nomenclature of Medicine ("SNOMED") data source, a Medical Dictionary for Regulatory Activities ("MedDRA") data source, or a World Health Organization ("WHO") drug data source. Adverse event report databases 678, 680, and 690 are data sources that include drug safety data, where the drug safety data includes one or more adverse event cases. However, these data sources are merely example data sources according to the illustrated embodiment, and in alternate embodiments, cohort identification system 600 can be operatively coupled to any number of data sources, and each data source can be any type of data source that includes data.

Cohort identification system 600 can further include federated query execution engine 685. Federated query execution engine 685 can allow a stored query to be compiled and be executed against multiple data sources. Federated query execution engine 685 can further merge the one or more case series returned from each data source into a single case series.

Cohort identification system 600 can also include flexible recategorization API 695. Flexible recategorization API 695 can normalize an interface to one or more code lists used in a data source. In most health related databases, discrete values are stored as codes. Code lists can be used to display one or more natural language equivalent terms. This feature can allow a user to specify query criteria in his, or her, own language. Further, one or more roll-up terms, such as "continent," can be used to refer to a group of discrete values, such as countries. Flexible recategorization API 695 can also allow one or more ranges of a continuous variable, such as age, to be mapped into one or more discrete named categories, such as "adult" or "child." Flexible recategorization API 695 can allow the same code mapping to be used in reporting, thus, ensuring consistency between the query and the reports.

Figure 7:
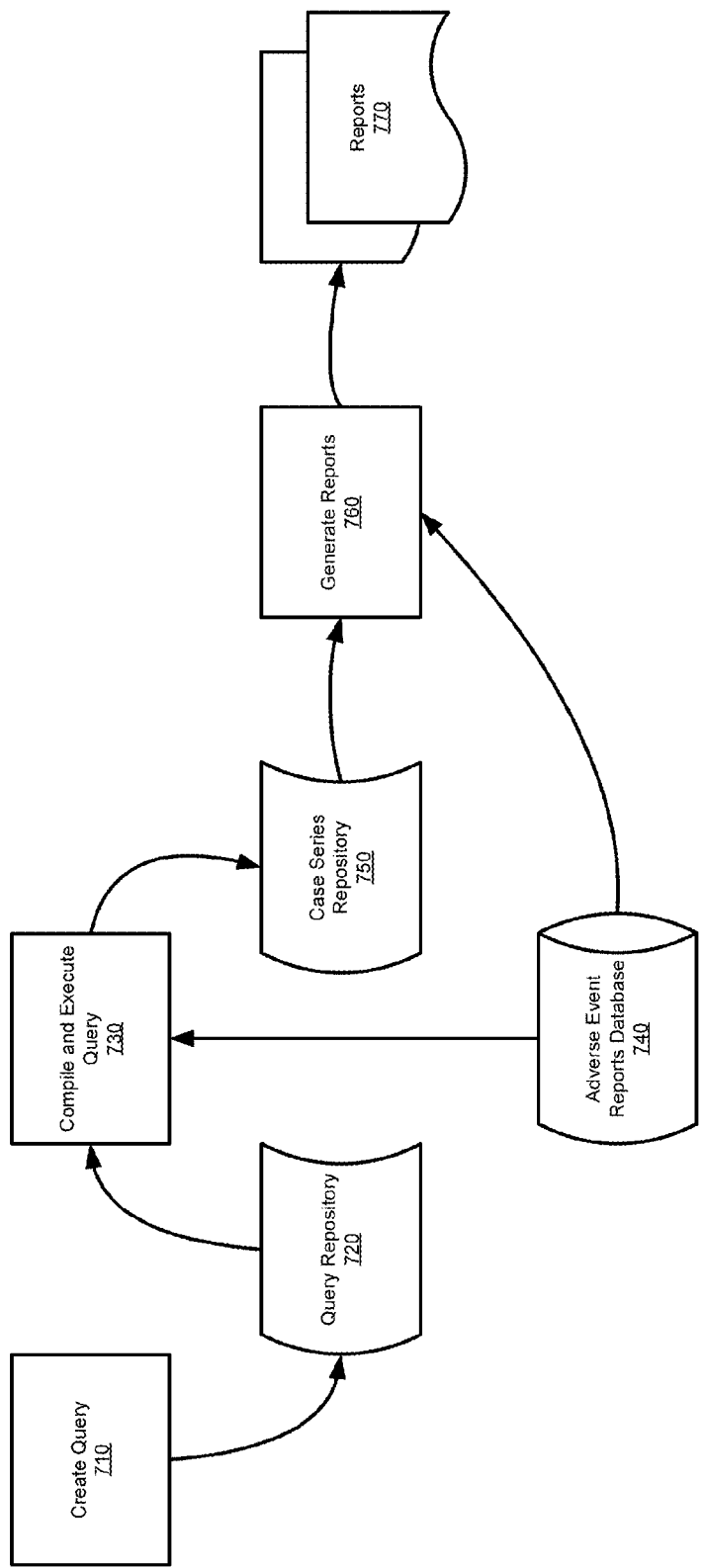
FIG. 7 illustrates a block diagram of an example implementation of a cohort identification system, according to an embodiment of the invention.

FIG. 7 illustrates a block diagram of an example implementation of a cohort identification system, according to an embodiment of the invention. At 710, a query is created. The query can be executed on a data source, such as a drug safety system, in order to retrieve data stored within the data source, such as drug safety data. According to the embodiment, in order to create the query, metadata can be retrieved, where the metadata describes the data within the data source. More specifically, the metadata can describe information about each data field of the data source that can be queried. Such information can include a data type of the data field and information required to construct a SQL query that include the data field. The query that is created is further stored at query repository 720, where query repository 720 is a repository that can store data, such as one or more queries.

At 730, a query is retrieved from query repository 720, where the query is compiled and executed on adverse event report database 740, an example of a data source. Adverse event report database 740 is a data source that includes drug safety data, where the drug safety data includes one or more adverse event cases. In executing the query, data, such as drug safety data, can be retrieved from adverse event report database 740. Further, in executing the query, a case series can be created and stored within case series repository 750.

At 760, the case series is retrieved from case series repository 750, and reports 770 are generated that can visualize the case series. According to an embodiment, a reporting case series API can interface with case series repository 750 and retrieve the case series from case series repository 750 and implement the case series within a reporting application, in order to generate the one or more reports that can visualize the case series, where the reporting application can display the generated one or more reports. In certain embodiments, the generation of reports that is performed at 760, can include retrieving data from adverse event report database 740.

Figure 8:
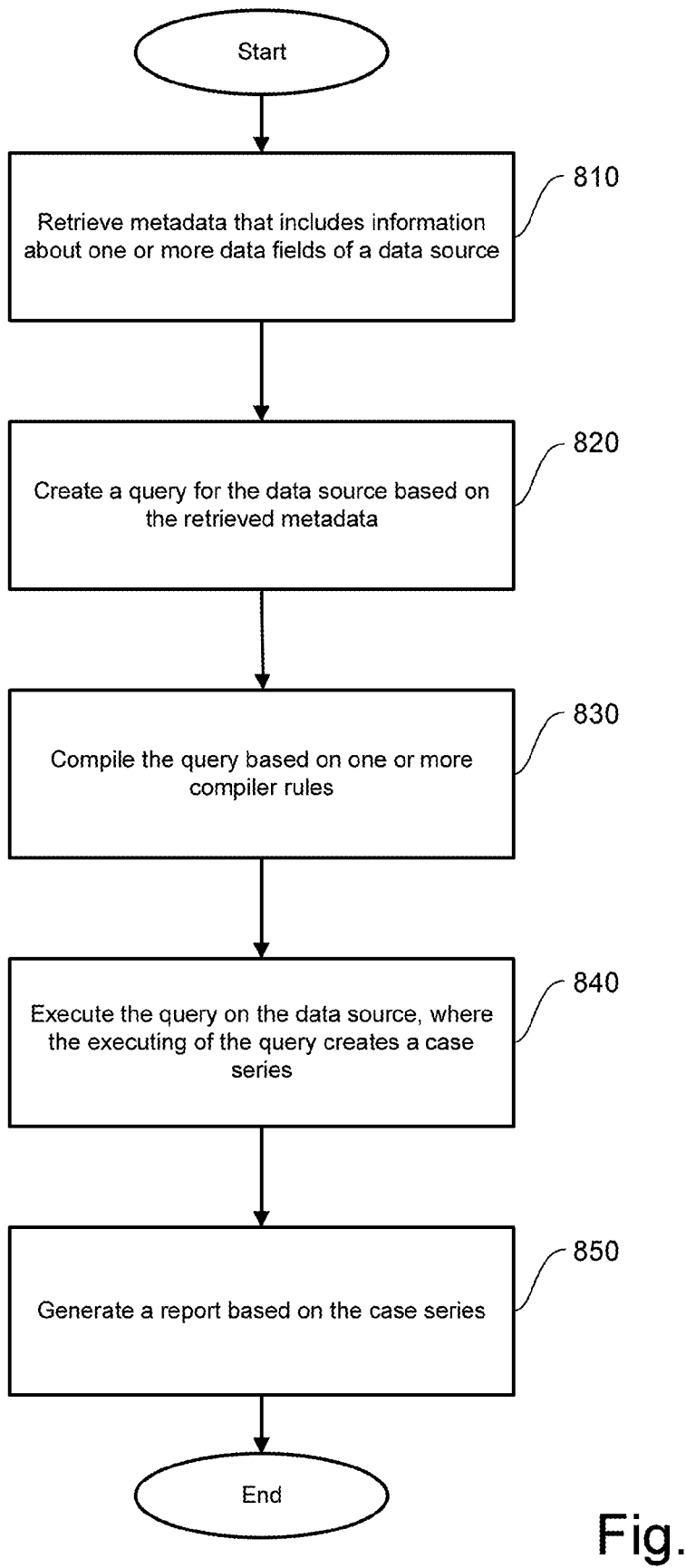
FIG. 8 illustrates a flow diagram of the functionality of a cohort identification module, according to an embodiment of the invention.

FIG. 8 illustrates a flow diagram of the functionality of a cohort identification module, according to an embodiment of the invention. The flow begins and proceeds to 810. The flow can begin when a user indicated that he, or she, wants to create a query. At 810, metadata is retrieved, where the metadata includes information about one or more data fields of a data source. According to the embodiment, the information can include a data type and SQL information for each data field of the one or more data fields. In certain embodiments, the data source can be an adverse event report database that stores one or more adverse event cases. The flow proceeds to 820.

At 820, a query is created for the data source based on the retrieved metadata. The query can be a query that is executed on a data source, in order to retrieve data stored within the data source. In certain embodiments, the retrieved metadata can be used to determine one or more data fields of the data source that are part of the query. Also, in certain embodiments, the retrieved metadata can be used to determine SQL that is part of the query. The flow proceeds to 830.

At 830, the query is compiled based on one or more compiler rules. According to the embodiment, compiler rules can include one or more syntax rules that are applied to the query to determine that the query complies with the one or more syntax rules. In certain embodiments, the query can be stored in a query repository. The flow proceeds to 840.

At 840, the query is executed on the data source, where the execution of the query creates a case series. In certain embodiments, the case series includes one or more adverse event cases, where each adverse event case includes a data record that represents an adverse event. In some of these embodiments, each data record that represents an adverse event further includes drug safety data, where drug safety data includes one or more reports or patient identifiers that are related to the safety of one or more drugs. In certain embodiments, the case series is stored in a case series repository. The flow proceeds to 850.

At 850, a report is generated based on the case series, where the report is a visualization of the case series. In certain embodiments, the report includes a visual display of one or more data fields of the case series. According to certain embodiments, the case series can be retrieved from the case series repository using a reporting case series API, where the reporting case series API defines a format of the case series for a reporting application. In these embodiments, the report can be displayed within the reporting application. Also, in certain embodiments, the case series can be retrieved from the case series repository using an interoperable case series API, where the interoperable case series API defines a format of the case series for a partner application. In these embodiments, the case series can be consumed within the partner application. The flow then ends.

Figure 9:
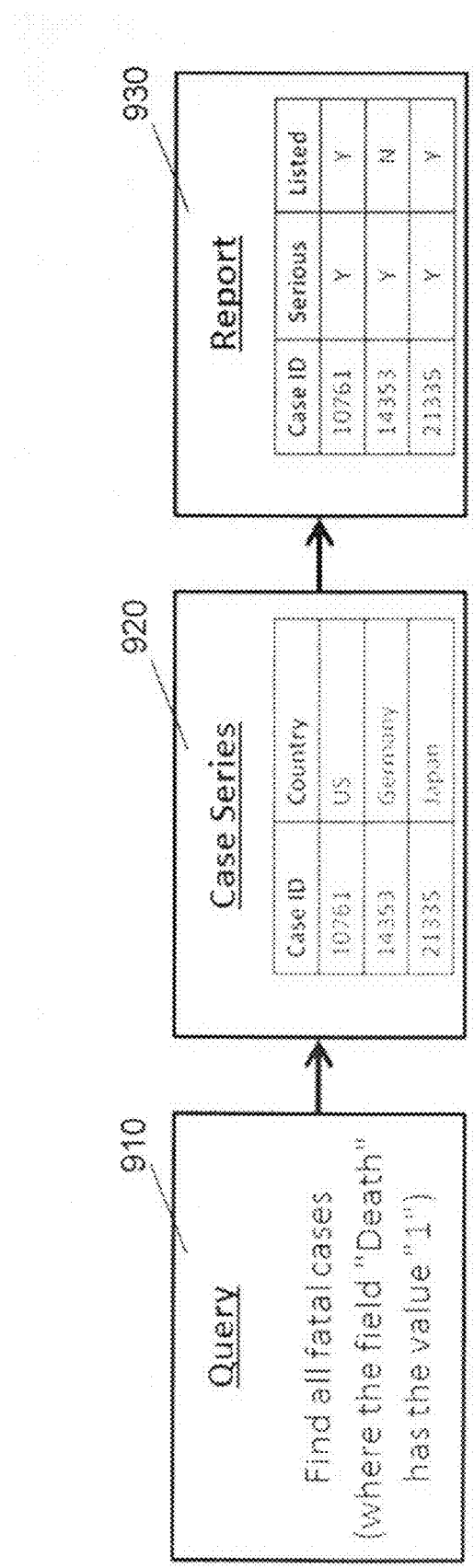
FIG. 9 illustrates an example query that creates an example case series that creates an example report, according to an embodiment of the invention.

FIG. 9 illustrates an example query 910 that creates an example case series 920 that creates an example report 930, according to an embodiment of the invention. According to an embodiment, an executable process can execute query 910 on a data source, such as a drug safety system, where query 910 is a query to retrieve all fatal adverse event cases (i.e., all adverse event cases where a data field "Death" has a value of 1).

The execution of query 910 produces case series 920, according to the embodiment, where case series 920 comprises a list of adverse event cases that matches the conditions specified in query 910. Case series 920 can include at least a case identifier for each adverse event case, and may also include additional case data or metadata that represent the adverse event cases in the case series. In the illustrated embodiment, case series 920 includes a plurality of adverse event cases, where each adverse event case includes: (a) a case identifier data field, where each value identifies a case identifier for the adverse event case; and (b) a country data field, where each value identifies a country that the adverse event case is associated with.

According to an embodiment, an executable process can generate report 930 based on case series 920. Report 930 is a visualization of case series 920, where the data fields of case series 920 can be changed depending on a desired format. In the illustrated embodiment, report 930 includes a plurality of adverse event cases, where each adverse event case includes: (a) a case identifier data field, where each value identifies a case identifier for the adverse event case; (b) a "serious" data field, where each value identifies whether the adverse event case is a serious adverse event case; and (c) a "listed" data field, where each value identifies whether the adverse event case is a listed adverse event case. One of ordinary skill in the art would readily appreciate that the formats of query 910, case series 920, and report 930 are example formats according to an example embodiment, and that queries, case series, and/or reports can have other formats in alternate embodiments.

As previously described, according to an embodiment, a point-in-time query system can be provided, where the point-in-time query system can provide an extensible framework that supports multiple point-in-time query types, where each point-in-time query type can utilize a different point-in-time query algorithm. The extensible framework can allow a user to select a point-in-time query type from one or more system-defined point-in-time query types using a user interface. The point-in-time query system can then create a point-in-time query based on the point-in-time query type selected by the user. Alternatively, the user can create and store one or more user-defined point-in-time query types that can utilize a user-defined point-in-time query algorithm. The user can then select a point-in-time query type from the one or more user-defined point-in-time query types, and create a point-in-time query based on the selected user-defined point-in-time query type using the user interface. The point-in-time query system can then execute the user-defined point-in-time query on the data source. By executing either a system-defined point-in-time query or a user-defined point-in-time query, the point-in-time query system can generate one or more cases that are part of a case series from one or more executed point-in-time queries and can store the one or more cases that are part of a case series in a case series repository.

According to an embodiment, a point-in-time query system can include metadata (such as metadata 610 of FIG. 6) that describes data within a data source, such as drug safety data within a drug system. The point-in-time query system can utilize the metadata to generate SQL for a point-in-time query, where the metadata can be utilized to generate one or more additional "WHERE clauses" of the SQL based on a selected point-in-time query type (which refers to a selected point-in-time query algorithm). The point-in-time query system can further include a user interface (such as query builder UI 605 of FIG. 6), where the user interface allows a user to select a system-defined point-in-time query type (or select a user-defined point-in-time query type that a user has previously created). According to the embodiment, the user interface can retrieve the metadata so that a user can create a point-in-time query based on the metadata using the user interface. Further, the point-in-time query system can include a repository (such as query repository 615 of FIG. 6) that can store one or more point-in-time queries. The point-in-time query system can further include a compiler (such as query compiler 620) that can retrieve a point-in-time query that is stored within the repository, and that can compile the stored point-in-time query. The point-in-time query system can then execute the compiled point-in-time query on a data source, retrieve data that is returned by the data source, create one or more case series based on the retrieved data (where each case series can include one or more cases). The point-in-time query can further store the one or more case series generated by the point-in-time query in a repository (such as case series repository 615 of FIG. 6), and can store information about the point-in-time query type (which can include the point-in-time query algorithm) used to generate the one or more case series.

In one embodiment, to support point-in-time queries, a data source can include one or more attributes to store "effective date information" (or valid date information) associated with each case, where each case can be a part of a case series. An example of effective date information is an effective start date (or valid start date) and an effective end date (or valid end date). An effective start date represents a date and/or time that a revision of a case was stored within the data source. An effective end date represents a date and/or time that a subsequent revision of the case was stored within the data source, where the subsequent revision replaces the previous revision. Thus, an effective end date of a revision of a case is the same value as an effective start date of a subsequent revision of the case. According to the embodiment, a current revision of a case can have an effective end date that is very far in the future (i.e., larger than any valid date and/or time). Also according to the embodiment, a revision of a case can be considered to be "effective" (or valid) from an effective start date up to, but not including, an effective end date (i.e., greater than or equal to an effective start date, and less than an effective end date). In one embodiment, a database table that stores one or more cases can include an EFFECTIVE_START_DATE column and an EFFECTIVE_END_DATE column that stores effective date information, where the EFFECTIVE_START_DATE column stores an effective start date for each case, and the EFFECTIVE_END_DATE column stores an effective end date for each case.

Further, according to the embodiment, the data source can include one or more attributes to store revision information associated with each case. An example of revision information is a "data lock point" ("DLP") revision number that represents a revision of a case, where a new revision of a case is generated and stored within the data source whenever the case is updated. Thus, each case that is stored within a data source can include a DLP revision number that identifies the revision of the case. In one embodiment, a database table that stores one or more cases can include a DLP_REVISION_NUMBER column that stores revision information, where the DLP_REVISION_NUMBER stored a revision number for each revision of each case. In addition, according to the embodiment, a data population process that populates the data source can populate the one or more attributes that stores the effective date information, and the one or more attributes that stores the revision information.

According to the embodiment, to further support point-in-time queries, a user interface can display an option for a user to select a point-in-time query type and a query "as-of date." More specifically, a user can select a point-in-time query type from one or more displayed system-defined point-in-time query types. Examples of system-defined point-in-time query types are further described below in greater detail. In one embodiment, where the user has created one or more user-defined point-in-time query types, the user can select a point-in-time query type from one or more displayed user-defined point-in-time query types as well. Further, a user can enter a date and/or time, where the entered date and/or time is used as the query as-of date. According to the embodiment, the query as-of date is used as a base date and is compared with an effective start date and an effective end date of one or more revisions of one or more cases, where the comparison is part of the point-in-time query. In an embodiment, a user can also select one or more attributes that are to be part of the point-in-time query.

According to the embodiment, when the point-in-query is executed, depending on the point-in-time query type, the point-in-time query is executed on one or more database tables of a data source and retrieves relevant data from the data source (i.e., one or more cases that satisfy the relevant criteria of the point-in-time query). In one embodiment, SQL is generated for the point-in-time query, where the SQL includes one or more relevant WHERE clauses based on the selected point-in-time query type. Subsequently, the one or more cases that are retrieved by the point-in-time query can be stored within a separate database table of the data source, along with their effective start dates and DLP revision numbers. An example of a separate database table is a CASE_DETAIL database table. Thus, the one or more cases can be stored for further analysis. In one embodiment, the one or more cases can be stored as part of a case series. Further, one or more reports can be executed based on the stored one or more cases. The one or more reports can be based on an effective start date and/or a DLP revision number. In an embodiment, each stored case series can be associated with a point-in-time query that generated the case series. Further, the one or more case series can be exported or imported into another system.

According to the embodiment, to further support point-in-time queries, the user interface can display criteria of a point-in-time query. More specifically, once query is executed, an option can be provided for the user interface to display the criteria of the point-in-time query, where the criteria can indicate a point-in-time query type that can be used. The user interface can also display an as of date or a last locked point-in-time associated with the point-in-time query. An example of a criteria display is shown below:
For As of Date Queries:
"As of Date: 01-Apr-2012 14:13:10
<Query Criteria>"
For Last Locked Point in Time Queries:
Last Locked Point In Time: 01-May-2012 10:13:00
<Query Criteria>

According to the embodiment, to further support point-in-time queries, the point-in-time query system can save a point-in-time query that is generated by a user within the data source. A user can subsequently select the saved point-in-time query and select a new point-in-time query type, so that a new point-in-time query of can be created, based on criteria of the saved point-in-time query and based on the new point-in-time query type. Further, a user can also select a new query as-of date for the new point-in-time query.

Examples of system-defined point-in-time query types are now described. However, in alternate embodiments, a point-in-time query system can utilize other system-defined point-in-time query types. A first example of a system-defined point in-time query type is a "current data query" type. A current data query is a point-in-time query that provides a consistent view of one or more current (i.e., most recent) revisions of one or more cases, regardless of whether the revisions of the one or more cases are "locked" or "unlocked." A revision of a case is "locked" when a status of the revision of the case is changed to a status that indicates that the revision of the case is an "official" revision, and that further modifications to the case will not be part of the "official" revision. A revision of a case is "unlocked" when the status of the revision of the case is any status other than a status that indicates that the revision of the case is an "official" revision. A base date of this type of point-in-time query is a current date. Thus, a current data query provides a view of a data source as it appears on the current date.

A second example of a system-defined point-in-time query type is a "last-locked-revision-as-of-a-point-in-time query" type. A last-locked-revision-as-of-a-point-in-time query is a point-in-time query that provides a consistent view of one or more last locked revisions (i.e., most recently locked revisions) of one or more cases on or before a specified point-in-time (e.g., an "as-of date"). A base date of a last-locked-revision-as-of-a-point-in-time query is a specified point-in-time (e.g., an as-of date). Thus, for each case, one or more last locked revisions (i.e., most recently locked revisions) of the case that were locked on or before the specified point-in-time (e.g., the as-of date) is returned by the last-locked-revision-as-of-a-point-in-time query. If there are any post-lock revisions to any of the one or more cases, the last-locked-revision-as-of-a-point-in-time query returns any post-lock revision data that is valid at the specified point-in time (e.g., the as-of date).

A third example of a system-defined point-in-time query type is a "last-locked-revision-for-a-version-in-a-period query" type. A last-locked-revision-for-a-version-in-a-period query is a point-in-time query that provides a consistent view of one or more last locked revisions (i.e., most recently locked revisions) for one or more versions of one or more cases in a time period. Two specified points in time (e.g., dates) are used to define the time period. Based on the defined time period, the last-locked revision-for-a-version-in-a-period query returns one or more last locked revisions (i.e., most recently locked revisions) of one or more versions of one or more cases, where the one or more versions of the one or more cases are within the defined time period. Any revisions that belong to versions of a case that are not included in the defined time period are not returned.

A fourth example of a system-defined point-in-time query type is an "at-submission query" type. An at-submission query is a point-in-time query that provides a consistent view of one or more locked revisions of one or more cases, as of a specified point-in-time (e.g., date) of a creation or submission of a report or submission associated with each case. A base date of at-submission query is a specified point-in-time (e.g., date) that a report or submission associated with one or more cases is created or submitted. Thus, an at-submission query can return multiple revisions of a case, where a report or submission associated with the case was created and/or submitted multiple times.

A fifth example of a system-defined point-in-time query type is an "at-lock query" type. An at-lock query is a point-in-time query that is a variant of an at-submission query, and that provides a consistent view of one or more locked revisions of one or more cases, as of a specified point-in-time (e.g., date) that each locked revision was locked. A base date of an at-lock query is a specified point-in-time (e.g., date) that a revision of one or more cases is locked. Thus, an at-lock query does not return any post-lock revisions of any cases. A list of lock dates (and/or times) can be provided, where a lock date (and/or time) records a user lock action. An at-lock query can use a valid start date (and/or time) and a valid end date (and/or time) of any locked revisions of any case.

A sixth example of a system-defined point-in-time query type is a "historic data query" type. A historic data query is a point-in-time query that is a variant of a current data query, and that provides a consistent view of one or more revisions of one or more cases, regardless of whether the revisions of the one or more cases are "locked" or "unlocked," where the revisions were current revisions as of a specified point-in-time (e.g., date). A base date of this type of point-in-time query is a specified point-in-time (e.g., an as-of date). Thus, a historical data query provides a view of a data source as it appears on the specified point-in-time (e.g., the as-of date).

Figure 10:
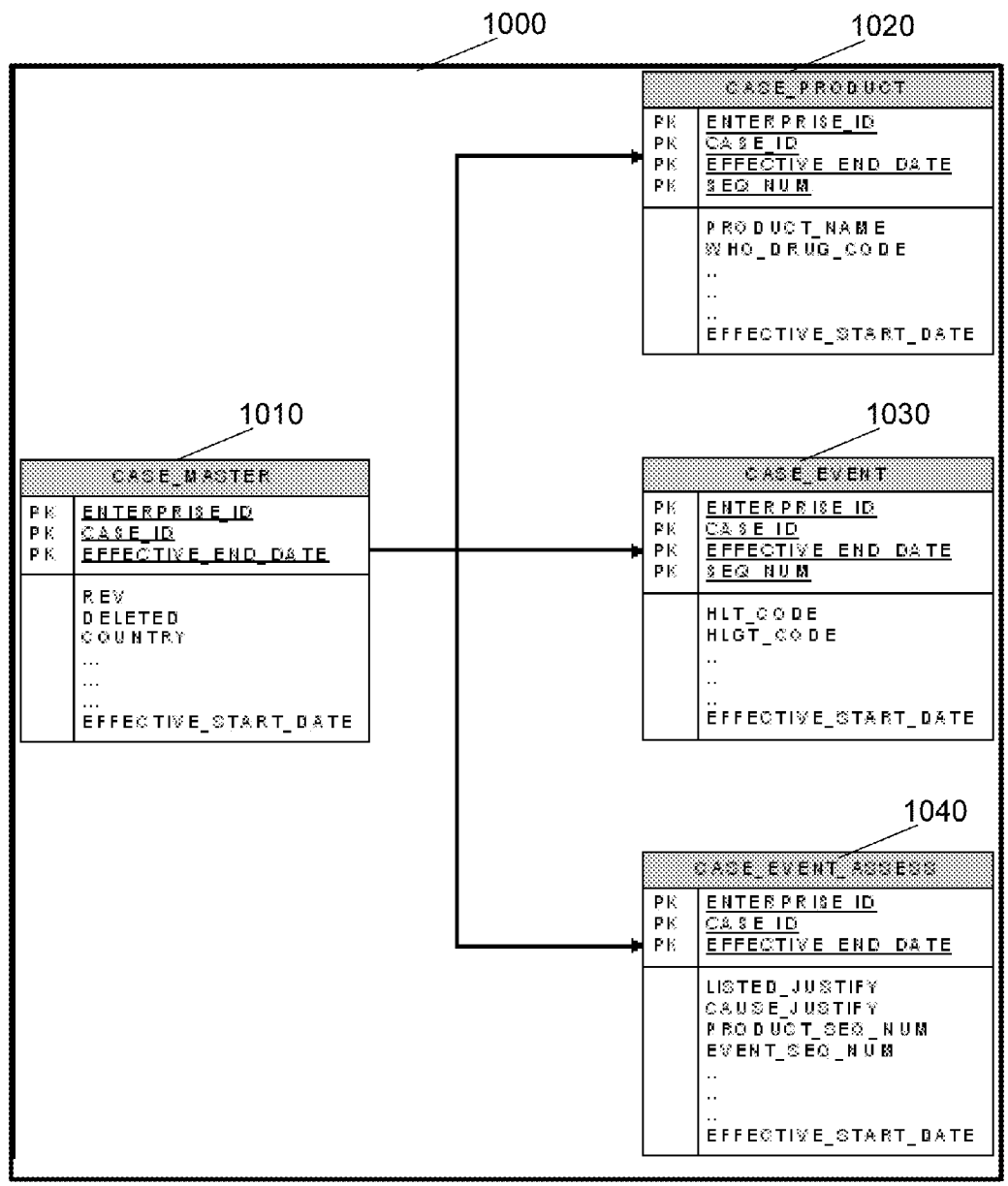
FIG. 10 illustrates an example data model that can support point-in-time querying, according to an embodiment of the invention.

FIG. 10 illustrates an example data model 1000 that can support point-in-time querying, according to an embodiment of the invention. More specifically, data model 1000 is an example data source that can store one or more versions of one or more cases series, and that can support point-in-time querying. According to the embodiments, data model 1000 can include effective date information that one or more point-in-time queries are executed on. More specifically, the effective date information can include an effective start date and an effective end date. As previously described, an effective start date represents a date and/or time that a revision of a case was stored within the data source, and an effective end date represents a date and/or time that a subsequent revision of the case was stored within the data source, where the subsequent revision replaces the previous revision. According to the embodiment, a current revision of a case can have an effective end date that is very far in the future (i.e., larger than any valid date and/or time). Also according to the embodiment, a revision of a case can be considered to be "effective" from an effective start date up to, but not including, an effective end date (i.e., greater than or equal to an effective start date, and less than an effective end date). Thus, there can be at least one revision of a case for each interval of time.

According to the embodiment, data model 1000 includes database tables 1010, 1020, 1030, and 1040. Database table 1010 (i.e., "CASE_MASTER") is a database table that can store one or more attributes associated with a revision of a case. One attribute of the one or more attributes can be an effective start date (i.e., "EFFECTIVE_START_DATE"), and another attribute of the one or more attributes can be an effective end date (i.e., "EFFECTIVE_END_DATE"). Database table 1020 (i.e., "CASE_PRODUCT") is a database table that can store one or more attributes associated with a product that is associated with revision of a case. One attribute of the one or more attributes can be an effective start date (i.e., "EFFECTIVE_START_DATE"), and another attribute of the one or more attributes can be an effective end date (i.e., "EFFECTIVE_END_DATE"). Database table 1030 (i.e., "CASE_EVENT") is a database table that can store one or more attributes associated with an event associated with a revision of a case. One attribute of the one or more attributes can be an effective start date (i.e., "EFFECTIVE_START_DATE"), and another attribute of the one or more attributes can be an effective end date (i.e., "EFFECTIVE_END_DATE"). Database table 1040 (i.e., "CASE_EVENT_ASSESS") is a database table that can store one or more attributes associated with an event assessment that is associated with a revision of a case. One attribute of the one or more attributes can be an effective start date (i.e., "EFFECTIVE_START_DATE"), and another attribute of the one or more attributes can be an effective end date (i.e., "EFFECTIVE_END_DATE"). Further, while data model 1000 is an example data source that can support point-in-time query, in alternate embodiments, other data sources that can support point-in-time query can be utilized by a point-in-time query system. Further, alternate data sources can use alternate data models, where the alternate data models include effective data information (e.g., an effective start date and an effective end date).

Figure 11:
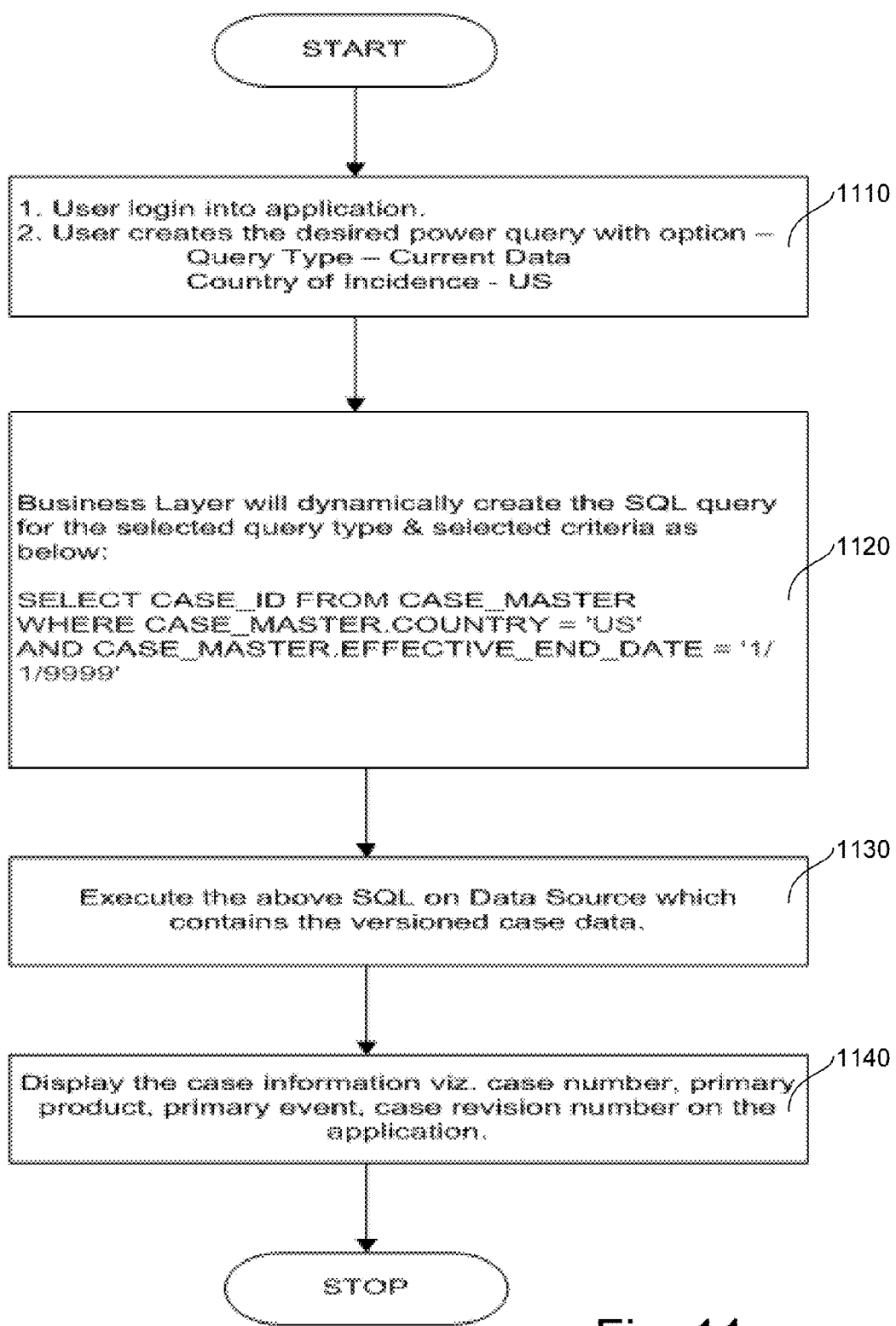
FIG. 11 illustrates a flow diagram of an example point-in-time query algorithm, according to an embodiment of the invention.
Figure 12:
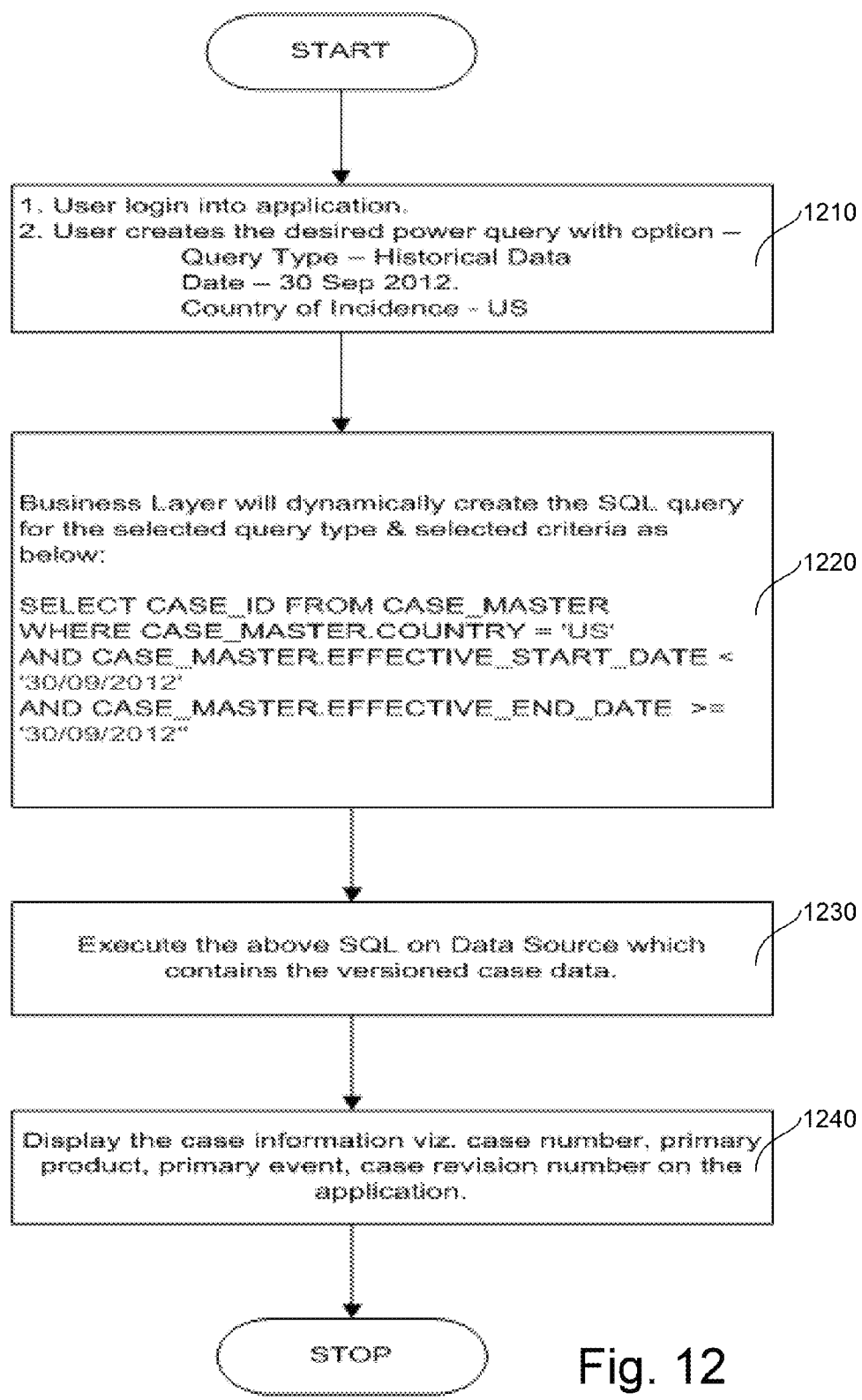
FIG. 12 illustrates a flow diagram of another example point-in-time query algorithm, according to another embodiment of the invention.
Figure 13:
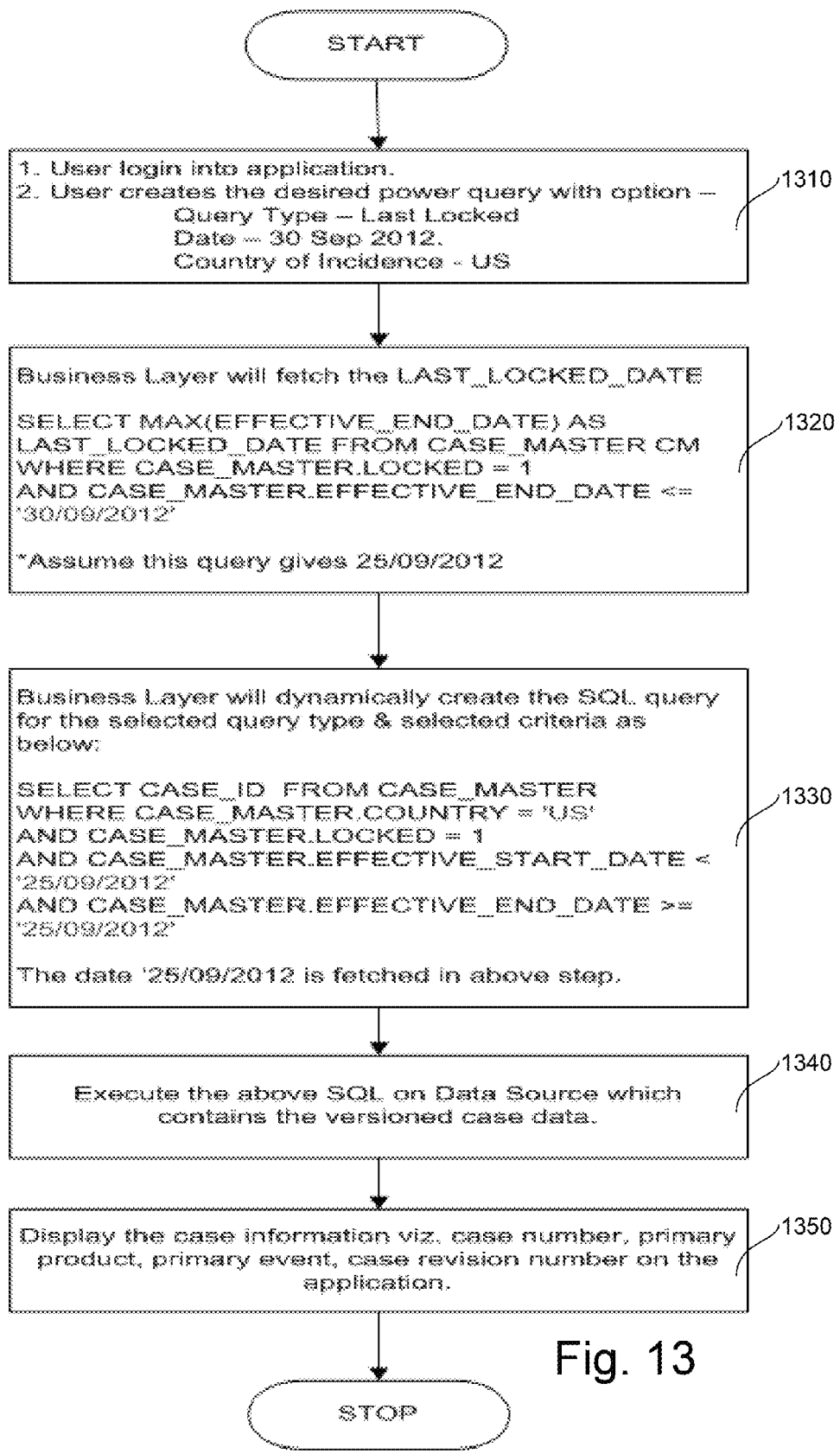
FIG. 13 illustrates a flow diagram of another example point-in-time query algorithm, according to another embodiment of the invention.

Example flows of example point-in-time query algorithms are now described in conjunction with FIGS. 11-13. However, one of ordinary skill in the art would readily appreciate that the following flows are example flows of example point-in-time query algorithms according to example embodiments, and that, in other alternate embodiments, a point-in-time query system can utilize a different point-in-time query algorithm within a different flow.

FIG. 11 illustrates a flow diagram of an example point-in-time query algorithm, according to an embodiment of the invention. According to the embodiment, the point-in time query algorithm is for a current data query (i.e., a point-in-time query whose query type is a current data query type), and a user wishes to utilize the current data query to retrieve a case series that includes one or more current cases where a country of incidence is the United States.

The flow begins and proceeds to 1110. At 1110, a user logs into a point-in-time query system (identified in FIG. 11 as an "application"), and the user creates a desired point-in-time query of a current data query type (identified in FIG. 11 as a "power query") using a user interface of the point-in-time query system. In creating the point-in-time query, the user selects a current data query type from one or more point-in-time query types displayed within a user interface, and selects the United States as a country of incidence. According to the embodiment, the user can select the United States as a country of incidence either by: (1) selecting the United States from one or more displayed countries of incidences; or (2) entering text within the user interface that identifies the United States as the country of incidence, such as "United States" or "US". The flow then proceeds to 1120.

At 1120, a business layer of the point-in-time query system dynamically creates an SQL query based on the selected query type and the selected criteria. A business layer of the point-in-time query system is further described below in greater detail. As illustrated in FIG. 11, an example SQL query that is dynamically created is "SELECT CASE_ID FROM CASE_MASTER WHERE CASE_MASTER.COUNTRY='US' AND CASE_MASTER.EFFECTIVE_END_DATE='1/1/9999'." According to the embodiment, the date "1/1/9999" is a "dummy value" (i.e., a value that is not a valid date). As previously described, a revision of a case that has such a value for its effective end date is a current revision of the case. Thus, the SQL query returns one or more current revisions of one or more cases where a country of incidence is the United States. The flow proceeds to 1130.

At 1130, the point-in-time query system executes the SQL query that is dynamically created at 1120 on a data source which contains one or more revisions of one or more cases. An example data source is data model 1000 of FIG. 10. The flow then proceeds to 1140.

At 1140, the point-in-time query system displayed the results of the SQL query that is executed at 1130 within the user interface. The results that are displayed within the user interface include information regarding one or more revisions of one or more cases that match the criteria of the SQL query (i.e., case series information). In one embodiment, the case series information displayed within the user interface includes a case number, a primary product, a primary event, and a revision number. The flow then ends.

FIG. 12 illustrates a flow diagram of another example point-in-time query algorithm, according to another embodiment of the invention. According to the embodiment, the point-in time query algorithm is for a historical data query type, and a user wishes to utilize the historical data query to retrieve a case series that includes one or more cases as of Sep. 30, 2012, where a country of incidence is the United States.

The flow begins and proceeds to 1210. At 1210, a user logs into a point-in-time query system (identified in FIG. 12 as an "application"), and the user creates a desired point-in-time query of a historic data query type (identified in FIG. 12 as a "power query") using a user interface of the point-in-time query system. In creating the point-in-time query, the user selects a historic data query type from one or more point-in-time query types displayed within a user interface, selects the date of Sep. 30, 2012 as a query as-of date, and selects the United States as a country of incidence. The user selects the date of Sep. 30, 2012 as a query as-of date either by: (1) selecting the date of Sep. 30, 2012 from one or more displayed dates; or (2) entering text within the user interface that identifies the date of Sep. 30, 2012 as the query as-of date, such as "09/30/2012," "30/09/2012," "9/30/12," or "Sep. 30, 2012." Similarly, the user selects the United States as a country of incidence either by: (1) selecting the United States from one or more displayed countries of incidences; or (2) entering text within the user interface that identifies the United States as the country of incidence, such as "United States" or "US". The flow then proceeds to 1220.

At 1220, a business layer of the point-in-time query system dynamically creates an SQL query based on the selected query type and the selected criteria. A business layer of the point-in-time query system is further described below in greater detail. As illustrated in FIG. 12, an example SQL query that is dynamically created is "SELECT CASE_ID FROM CASE_MASTER WHERE CASE_MASTER.COUNTRY='US' AND CASE_MASTER.EFFECTIVE_START_DATE<'30/09/2012' AND CASE_MASTER.EFFECTIVE_END_DATE>='30/09/2012'." According to the embodiment, the SQL query includes a condition regarding an effective start date and a condition regarding an effective end date. Thus, the SQL query returns one or more revisions of one or more cases as of Sep. 30, 2012, where a country of incidence is the United States. The flow proceeds to 1230.

At 1230, the point-in-time query system executes the SQL query that is dynamically created at 1220 on a data source which contains one or more revisions of one or more cases. An example data source is data model 1000 of FIG. 10. The flow then proceeds to 1240.

At 1240, the point-in-time query system displayed the results of the SQL query that is executed at 1230 within the user interface. The results that are displayed within the user interface include information regarding one or more revisions of one or more cases that match the criteria of the SQL query (i.e., case series information). In one embodiment, the case series information displayed within the user interface includes a case number, a primary product, a primary event, and a revision number. The flow then ends.

FIG. 13 illustrates a flow diagram of another example point-in-time query algorithm, according to another embodiment of the invention. According to the embodiment, the point-in time query algorithm is for a last-locked-revision-as-of-a-point-in-time query type, and a user wishes to utilize the last-locked-revision-as-of-a-point-in-time query to retrieve a case series that includes one or more last locked cases as of Sep. 30, 2012, where a country of incidence is the United States. Thus, in other words, the user wishes to utilize the last-locked revision-as-of-a-point-in-time query to retrieve one or more most recent versions of one or more cases that were locked on or before Sep. 30, 2012. As previously described, a revision of a case is "locked" when a status of the revision of the case is changed to a status that indicates that the revision of the case is an "official" revision, and that further modifications to the case will not be part of the "official" revision. A revision of a case is "unlocked" when the status of the revision of the case is any status other than a status that indicates that the revision of the case is an "official" revision.

The flow begins and proceeds to 1310. At 1310, a user logs into a point-in-time query system (identified in FIG. 13 as an "application"), and the user creates a desired point-in-time query of a last-locked-revision-as-of-a-point-in-time query type (identified in FIG. 13 as a "power query") using a user interface of the point-in-time query system. In creating the point-in-time query, the user selects a last-locked-revision-as-of-a-point-in-time query type from one or more point-in-time query types displayed within a user interface, selects the date of Sep. 30, 2012 as a query as-of date, and selects the United States as a country of incidence. The user selects the date of Sep. 30, 2012 as a query as-of date either by: (1) selecting the date of Sep. 30, 2012 from one or more displayed dates; or (2) entering text within the user interface that identifies the date of Sep. 30, 2012 as the query as-of date, such as "09/30/2012," "30/09/2012," "9/30/12," or "Sep. 30, 2012." Similarly, the user selects the United States as a country of incidence either by: (1) selecting the United States from one or more displayed countries of incidences; or (2) entering text within the user interface that identifies the United States as the country of incidence, such as "United States" or "US". The flow then proceeds to 1320.

At 1320, a business layer of the point-in-time query system fetches a last locked date as of Sep. 30, 2012. A business layer of the point-in-time query system is further described below in greater detail. As illustrated in FIG. 13, an example SQL query that is used to fetch the last locked date as of Sep. 30, 2012, is "SELECT MAX(EFFECTIVE_END_DATE) AS LAST_LOCKED_DATE FROM CASE_MASTER CM WHERE CASE_MASTER_LOCKED=1 AND CASE_MASTER.EFFECTIVE_END_DATE<='30/09/12'." According to the embodiment, the example SQL query returns a value of "25/09/2012." This value is used in the SQL query that is dynamically generated at 1330, as is described below in greater detail. The flow then proceeds to 1330.

At 1330, the business layer of the point-in-time query system dynamically creates an SQL query based on the selected query type and the selected criteria. As illustrated in FIG. 13, an example SQL query that is dynamically created is "SELECT CASE_ID FROM CASE_MASTER WHERE CASE_MASTER.COUNTRY='US' AND CASE_MASTER.LOCKED=1 AND CASE_MASTER.EFFECTIVE_START_DATE<'25/09/2012' AND CASE_MASTER.EFFECTIVE_END_DATE>='25/09/2012'." According to the embodiment, the SQL query includes a condition regarding an effective state date and a condition regarding an effective end date, where each condition utilizes the value of "25/09/2012" that was fetched by the SQL query of 1320. Thus, the SQL query returns one or more most recent versions of one or more cases that were locked on or before Sep. 30, 2012, where a country of incidence is the United States. The flow proceeds to 1340.

At 1340, the point-in-time query system executes the SQL query that is dynamically created at 1330 on a data source which contains one or more revisions of one or more cases. An example data source is data model 1000 of FIG. 10. The flow then proceeds to 1350.

At 1350, the point-in-time query system displayed the results of the SQL query that is executed at 1340 within the user interface. The results that are displayed within the user interface include information regarding one or more revisions of one or more cases that match the criteria of the SQL query (i.e., case series information). In one embodiment, the case series information displayed within the user interface includes a case number, a primary product, a primary event, and a revision number. The flow then ends.

According to certain embodiments, a point-in-time query system can include a database layer and a business layer. The point-in-time query system can utilize the database layer and the business layer to create a SQL query for one or more point-in-time query types. According to the embodiments, the database layer and the business layer are both metadata components. In some of the embodiments, the database layer is a component similar to metadata 610 of FIG. 6, and the business layer is a component similar to query compiler 620 of FIG. 6.

According to certain embodiments, the database layer includes two metadata tables that support point-in-time querying. More specifically, the two metadata tables store metadata that can be used by the business layer to dynamically create a SQL query associated with a point-in-time query. In some of these embodiments, these two metadata tables are metadata tables that are added to metadata 610 of FIG. 6.

Further, in some of these embodiments, the first metadata table is a table that includes metadata that identifies each point-in-time query that has been created within the point-in-time query system. Each point-in-time query can be either a system-defined point-in-time query or a user-defined point-in-time query. An example metadata table is included below.

| QUERY_TYPE_ID | QUERY_TYPE_NAME |
|---|---|
| 1 | CURRENT_DATA |
| 2 | HISTORICAL_DATA |
| 3 | LAST_LOCKED_DATA |

In the example metadata table, QUERY_TYPE_ID stores an identity of a point-in-time query type, and QUERY_TYPE_NAME stores a name of point-in-time query type. In the above example: (a) the identity "1," and the name "CURRENT_DATA" refer to a current data query type; (b) the identity "2," and the name "HISTORICAL_DATA," refer to a historical data query type; and (c) the identity "3," and the name "LAST_LOCKED_DATA" refer to a last-locked-revision-as-of-a-point-in-time query type. However, one of ordinary skill in the art would readily appreciate that the above example is an example embodiment, and that in other alternate embodiments, the metadata table can also store an identity and a name for a last-locked-revision-for-a-version-in-a-period query type, an at-submission query type, an at-lock query type, any other system-defined point-in-time query type, or any user-defined point-in-time query type.

In some of these embodiments, the second metadata table is a table that includes metadata that can be used to create a SQL query for a point-in-time query. More specifically, the table includes one or more relevant WHERE clauses for a SQL query associated with a point-in-time query. Each set of one or more WHERE clauses can be associated with an identity of a query type. An example metadata table is included below:

In the example metadata table, QUERY_TYPE_ID stores an identity of a point-in-time query type, and ADDITIONAL_WHERE stores one or more additional WHERE clauses that are part of a SQL query that can be created for point-in-time query type.

In the above example: (a) the WHERE clause, "AND TABLE.EFFECTIVE_END_DATE='1/1/9999'," is part of a SQL query that can be created for a current data query type (where "1/1/9999" is a dummy value); (b) the WHERE clauses, "AND TABLE.EFFECTIVE_START_DATE<:USER_DATE," and "AND TABLE.EFFECTIVE_END_DATE>=:USER_DATE," are part of a SQL query that can be created for a historical data query type (where ":USER_DATE" is a date supplied by a user of the point-in-time query system); and (c) the WHERE clauses, "AND TABLE.EFFECTIVE_START_DATE<(SELECT MAX (EFFECTIVE_END_DATE) FROM CASE_MASTER X WHERE CASE_MASTER.LOCKED=1 AND X.CASE_ID=TABLE.CASE_ID AND CASE_MASTER.EFFECTIVE_END_DATE<=:USER_DATE)," and "AND TABLE.EFFECTIVE_END_DATE>=(SELECT MAX (EFFECTIVE_END_DATE) FROM CASE_MASTER X WHERE CASE_MASTER_LOCKED=1 AND X.CASE_ID=TABLE.CASE_ID AND CASE_MASTER.EFFECTIVE_END_DATE<=:USER_DATE)," are part of a SQL query that can be created for a last-locked-revision-as-of-a-point-in-time query type (where ":USER_DATE" is a date supplied by a user of the point-in-time query system).

However, one of ordinary skill in the art would readily appreciate that the above example is an example embodiment, and that in other alternate embodiments, the metadata table can also store an identity and one or more additional WHERE clauses for a last-locked-revision-for-a-version-in-a-period query type, an at-submission query type, an at-lock query type, any other system-defined point-in-time query type, or any user-defined point-in-time query type.

According to certain embodiments, the business layer includes logic that adds one or more WHERE clauses to a SQL query that is generated for a point-in-time query. In some of the embodiments, the logic of the business layer is logic that is added to query compiler 620 of FIG. 6.

Further, in some of the embodiments, the logic of the business layer populates a list of tables based on one or more criteria selected by a user for a point-in-time query. In one embodiment, the data that is populated in the list of tables is fetched from a metadata table. An example of such a metadata table is a database table CMN_FIELDS, which is a database table that stores the metadata that maps a criteria to a table and

| QUERY_TYPE_ID | ADDITIONAL_WHERE |
|---|---|
| 1 | AND TABLE.EFFECTIVE_END_DATE = '1/1/9999' |
| 2 | AND TABLE.EFFECTIVE_START_DATE < :USER_DATE<br>AND TABLE.EFFECTIVE_END_DATE >= :USER_DATE |
| 3 | AND TABLE.EFFECTIVE_START_DATE <<br>(SELECT MAX (EFFECTIVE_END_DATE)<br>  FROM CASE_MASTER X<br>  WHERE CASE_MASTER.LOCKED = 1<br>  AND X.CASE_ID = TABLE.CASE_ID<br>  AND CASE_MASTER.EFFECTIVE_END_DATE<br>  <=:USER_DATE)<br>AND TABLE.EFFECTIVE_END_DATE >=<br>(SELECT MAX (EFFECTIVE_END_DATE)<br>  FROM CASE_MASTER X<br>  WHERE CASE_MASTER_LOCKED = 1<br>  AND X.CASE_ID = TABLE.CASE_ID<br>  AND CASE_MASTER.EFFECTIVE_END_DATE<br>  <= :USER_DATE) | that maps a table to a column. Based on one or more criteria selected by the user for the point-in-time query, the logic of the business layer dynamically constructs a WHERE clause of a SQL query using the metadata table (e.g., database table CMN_FIELDS). Further, based on a point-in-time query type selected by a user, the logic of the business layer can fetch one or more additional WHERE clauses from an ADDITIONAL_WHERE column of a QUERY_TYPE_CONFIGURATION table.

According to the embodiment, for each table in the table list, the logic of the business layer can add the one or more additional WHERE clauses to the WHERE clause of the SQL query, where an actual table name is substituted for a "TABLE" string in the fetched one or more additional WHERE clauses. For example, if a table list contains the tables CASE_MASTER and CASE_PRODUCT, and a selected point-in-time query type is a current data query, then the additional WHERE clause is "CASE_MASTER.END_DATE='1/1/9999' AND CASE_PRODUCT.END_DATE='1/1/9999'." For a historical data query type, in addition to a substitution of an actual table name, a date supplied by a user is also substituted for a ":USER_DATE" variable in the fetched one or more additional WHERE clauses. Further, for a last-locked-revision-as-of-a-point-in-time query type, an additional SQL query can be generated to retrieve a last locked date (e.g., LAST_LOCKED_DATE) based on a date entered by a user. This last locked date is then substituted for a ":LAST_LOCKED_DATE" variable in the fetched one or more additional WHERE clauses. Further, because a design of the business layer is metadata-driven, the logic of the business layer can support additional point-in-time query types (such as, a last-locked-revision-for-a-version-in-a-period query type, an at-submission query type, an at-lock query type, any other system-defined point-in-time query type, or any user-defined point-in-time query type), after the appropriate metadata is entered in the metadata tables of the database layer (e.g., database tables QUERY_TYPE_MASTER and QUERY_TYPE_CONFIGURATION), as previously described.

Figure 14:
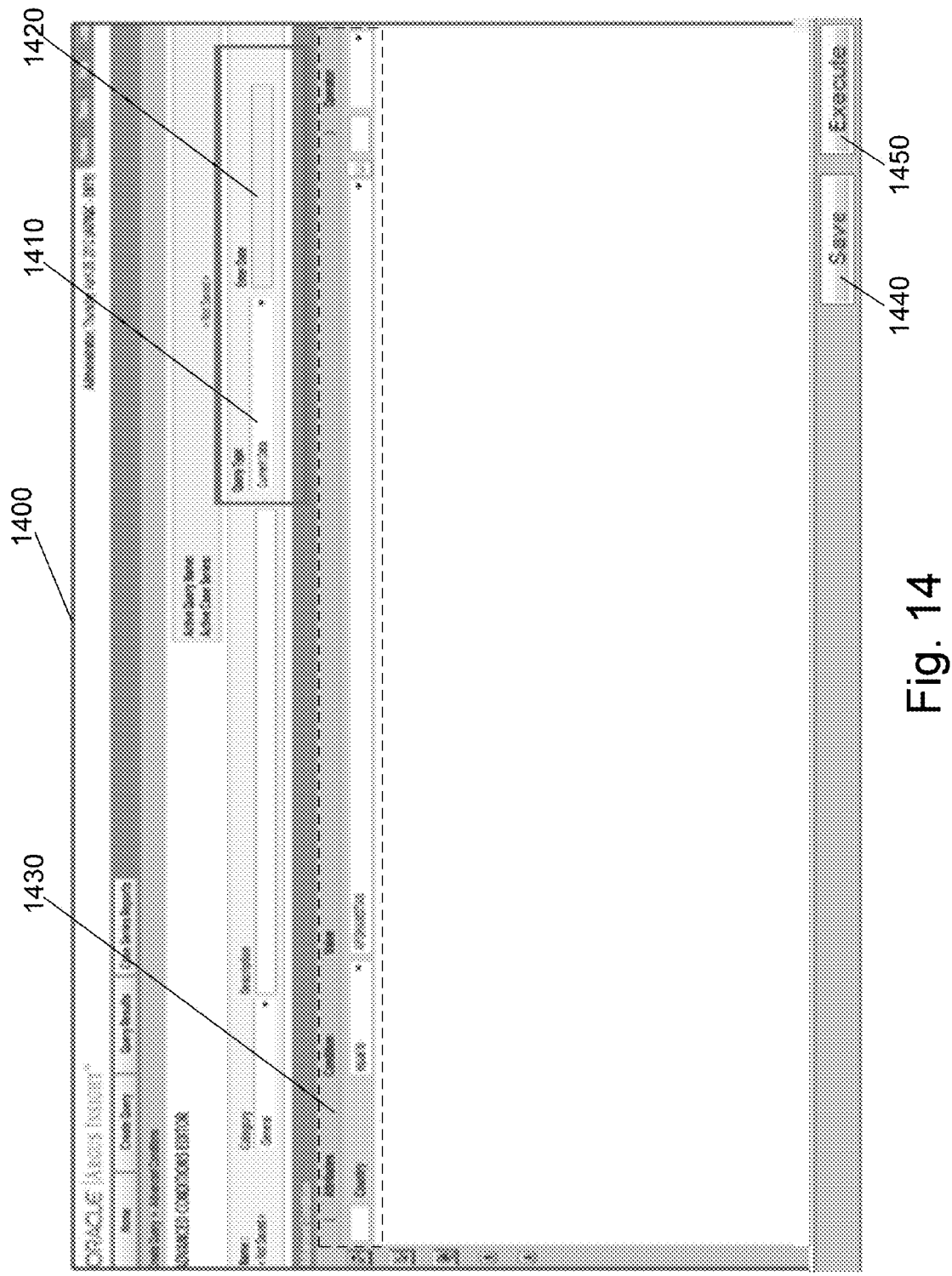
FIG. 14 illustrates an example user interface of a point-in-time query system, according to an embodiment of the invention.

FIG. 14 illustrates an example user interface 1400 of a point-in-time query system, according to an embodiment of the invention. According to the embodiment, user interface 1400 is a query editor user interface that allows a user to create and/or a point-in-time query. User interface 1400 includes query type 1410. Query type 1410 can display a list of one or more point-in-time query types, where a point-in-time query type can be a system-defined point-in-time query type or a user-defined point-in-time query type. A user can select a point-in-time query type from the list of one or more point-in-time query types displayed within query type 1410. User interface 1400 further includes enter date 1420. A user can enter a date and/or time within enter date 1420 (if required by the selected query type displayed within query type 1410), where the date and/or time is the as-of query date for the point-in-time query. Further, user interface 1400 displays attributes 1430. A user can select one or more attributes within attributes 1430 to be part of the point-in-time query. User interface 1400 further includes save 1440 and execute 1450. A user can save the point-in-time query by selecting save 1440, or execute the point-in-time query by selecting execute 1450. Further, a user can select a point-in-time query that has been previously saved within user interface 1400, and execute the query by selecting execute 1450. One of ordinary skill in the art would readily appreciate that user interface 1400 is an example user interface for creating and/or editing a point-in-time query, and that, in alternate embodiments, user interface 1400 may have a different appearance.

Figure 15:
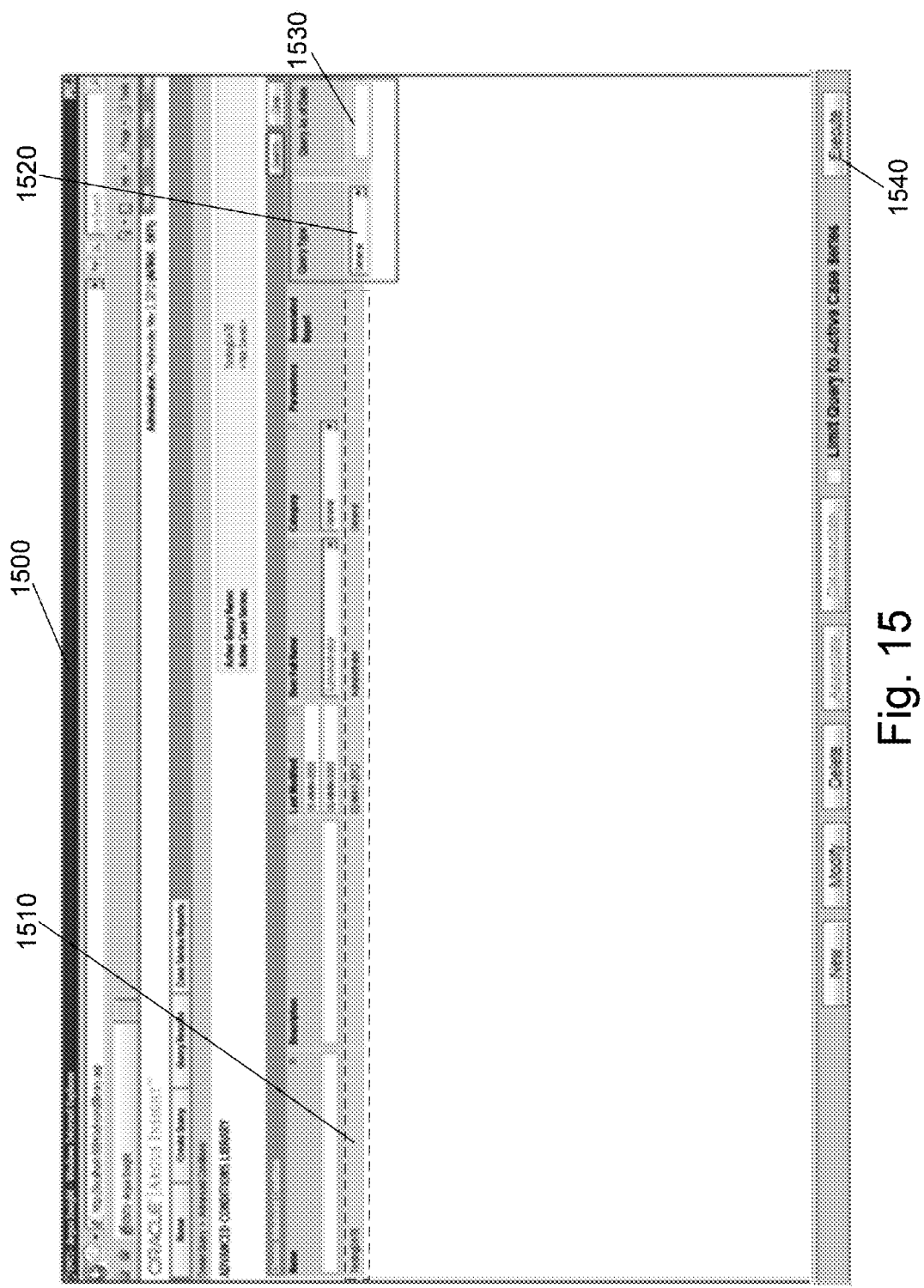
FIG. 15 illustrates another example user interface of a point-in-time query system, according to another embodiment of the invention.

FIG. 15 illustrates another example user interface 1500 of a point-in-time query system, according to another embodiment of the invention. According to the embodiment, user interface 1500 is a query library user interface that allows a user to select an existing point-in-time query to execute. User interface 1500 can further allow the user to edit the existing point-in-time query before executing the existing point-in-time-query. User interface 1500 includes query 1510. Query 1510 displays one or more point-in-time queries that have been saved using a user interface (such as user interface 1400 of FIG. 14). User interface 1500 further includes query type 1520 and query as-of date 1530. Query type 1520 displays a point-in-time query type associated with a corresponding point-in-time query. According to the embodiment, a user can select a new point-in-time query type from a list of one or more point-in-time query types displayed within query type 1520, and thus, can modify a point-in-time query type associated with the point-in-time query. Query as-of date 1530 displays a query as-of date associated with a corresponding point-in-time query (if a query as-of date is associated with the point-in-time query). According to the embodiment, a user can enter a new date and/or time within query as-of date 1530, and thus, can modify a query as-of date associated with the point-in-time query (or associate a query as-of date with the point-in-time query, if the point-in-time query was not previously associated with a query as-of date). User interface 1500 further includes execute 1540. A user can execute a selected point-in-time query displayed within query 1510 by selecting execute 1540. One of ordinary skill in the art would readily appreciate that user interface 1500 is an example user interface for creating and/or editing a point-in-time query, and that, in alternate embodiments, user interface 1500 may have a different appearance.

Figure 16:
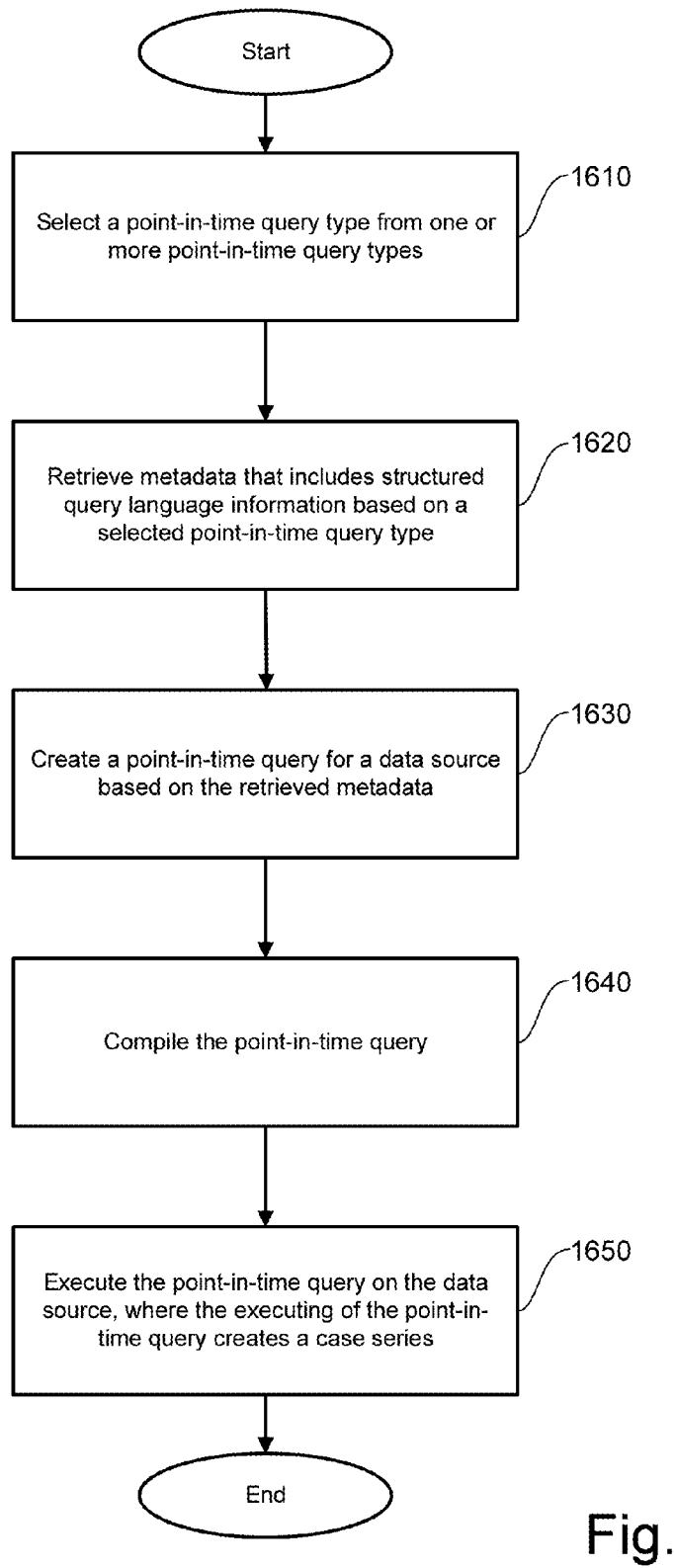
FIG. 16 illustrates a flow diagram of the functionality of a point-in-time query module, according to an embodiment of the invention.

FIG. 16 illustrates a flow diagram of the functionality of a point-in-time query module, according to an embodiment of the invention. The flow begins and proceeds to 1610. The flow can begin when a user indicated that he, or she, wants to create a point-in-time query. At 1610, a point-in-time query type is selected from one or more point-in-time query types. In certain embodiments, the one or more point-in-time query types can include at least one of: a system-defined point-in-time query type; or a user-defined point-in-time query type. In some of these embodiments, the system-defined point-in-time query type can be one of: a current data query type; a last-locked-revision-as-of-a-point-in-time query type; a last-locked-revision-for-a-version-in-a-period query type; an at-submission query type; an at-lock query type; or a historical data query type.

Further in certain embodiments, a user-defined point-in-time query type can be defined by a user when the user: (1) creates the user-defined point-in-time query type; (2) creates metadata associated with the user-defined point-in-time query type, where the metadata includes SQL information; and (3) stores the created metadata, where the created metadata is associated with the user-defined point-in-time query type. In certain embodiments, in addition to selecting a point-in-time query type, a date and/or time can also be selected. The flow then proceeds to 1620.

At 1620, metadata is retrieved, where the metadata includes SQL information that is based on the selected point-in-time query type. In certain embodiments, the SQL information that is based on the selected point-in-time query type can include one or more WHERE clauses that are based on the selected point-in-time query type. In certain embodiments, the metadata can further information about one or more data fields of a data source. According to the embodiment, the information can include a data type and SQL information for each data field of the one or more data fields. In certain embodiments, the data source can be an adverse event report database that stores one or more adverse event cases. The flow then proceeds to 1630.

At 1630, a point-in-time query is created for the data source based on the retrieved metadata, where the point-in-time query is a query that is based on a date and/or time. The point-in-time query can be a query that is executed on a data source, in order to retrieve data stored within the data source. In certain embodiments, the retrieved metadata can be used to determine one or more data fields of the data source that are part of the query. Also, in certain embodiments, the retrieved metadata can be used to determine SQL that is part of the query.

In certain embodiments where a date and/or time are selected, the point-in-time query can be created based on the selected date and/or time. In these embodiments, the SQL information can be combined with the selected date and/or time. The flow then proceeds to 1640.

At 1640, the point-in-time query is compiled. In certain embodiments, the point-in-time query can be compiled based on one or more compiler rules. According to the embodiment, compiler rules can include one or more syntax rules that are applied to the point-in-time query to determine that the point-in-time query complies with the one or more syntax rules. In certain embodiments, the point-in-time query can be stored in a query repository. The flow then proceeds to 1650.

At 1650, the point-in-time query is executed on the data source, where the execution of the point-in-time query creates a case series. In certain embodiments, the case series includes one or more adverse event cases, where each adverse event case includes a data record that represents an adverse event. In some of these embodiments, each data record that represents an adverse event further includes drug safety data, where drug safety data includes one or more reports or patient identifiers that are related to the safety of one or more drugs. In certain embodiments, the case series is stored in a case series repository.

Further, in some embodiments where the point-in-time query is stored within the query repository, the point-in-time query can be modified by modifying at least one of: (1) a point-in-time query type associated with the stored point-in-time query; or (2) a date and/or time associated with the stored point-in-time query. The modified point-in-time query can then be executed. The flow then ends.

Thus, in one embodiment, a point-in-time query system is provided that can create one or more point-in-time queries based on retrieved metadata. The point-in-time query system can support multiple point-in-time query types within a single extensible framework, where the framework can be extended to support one or more user-defined point-in-time query types. Further, the point-in-time query system is able to support the multiple point-in-time query types without modifying computer program code due to the metadata associated with each point-in-time query type. Thus, the point-in-time query system can provide a single user interface and framework which can support different types of point-in-time query algorithms, helping users to utilize a set of point-in-time query algorithms and providing results for different analysis needs. Such a feature set can be a more complete and flexible feature set than is available in any single application. The point-in-time query system can further provide the flexibility of using a point-in-time query for different results without duplicating the point-in-time query, and can further use the resulting case series for different reporting needs. This can result in reduced cost and time based on the removal of effort in duplicating queries.

The features, structures, or characteristics of the invention described throughout this specification may be combined in any suitable manner in one or more embodiments. For example, the usage of "one embodiment," "some embodiments," "certain embodiment," "certain embodiments," or other similar language, throughout this specification refers to the fact that a particular feature, structure, or characteristic described in connection with the embodiment may be included in at least one embodiment of the present invention. Thus, appearances of the phrases "one embodiment," "some embodiments," "a certain embodiment," "certain embodiments," or other similar language, throughout this specification do not necessarily all refer to the same group of embodiments, and the described features, structures, or characteristics may be combined in any suitable manner in one or more embodiments.

One having ordinary skill in the art will readily understand that the invention as discussed above may be practiced with steps in a different order, and/or with elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. A non-transitory computer-readable medium having instructions stored thereon that, when executed by a processor, cause the processor to implement a point-in-time query, the implementing comprising:
   receiving a selection of a point-in-time query type, from one or more point-in-time query types, from a user;
   retrieving metadata, from a repository, that comprises structured query language information based on the selected point-in-time query type;
   creating a point-in-time query for a drug safety database based on the retrieved metadata and a date, the drug safety database including a plurality of adverse event records, each adverse event record including an effective end date indicating when a subsequent revision of the adverse event record was stored in the drug safety database, a patient identifier and drug safety data associated with a patient, the point-in-time query including a comparison of the date with the adverse event record effective end date;
   compiling the point-in-time query to create a compiled point-in-time query; and
   executing the compiled point-in-time query on the drug safety database to create a case series.

2. The non-transitory computer-readable medium of claim 1, the implementing further comprising:
   receiving a selection of the date from the user,
   wherein each adverse event record includes an effective start date indicating when the adverse event record was stored in the drug safety database, and
   wherein the point-in-time query further includes a comparison of the date with the adverse event record effective start date.

3. The non-transitory computer-readable medium of claim 1, the implementing further comprising:
   creating a user-defined point-in-time query type;
   creating metadata, associated with the user-defined point-in-time query type, including structured query language information; and
   storing the created metadata in the repository.

4. The non-transitory computer-readable medium of claim 1, wherein the one or more point-in-time query types comprises at least one of:
a system-defined point-in-time query type; or
a user-defined point-in-time query type.

5. The non-transitory computer-readable medium of claim 4, wherein the system-defined point-in-time query type is one of:
a current data query type;
a last-locked-revision-as-of-a-point-in-time query type;
a last-locked-revision-for-a-version-in-a-period query type;
an at-submission query type;
an at-lock query type; or
a historical data query type.

6. The non-transitory computer-readable medium of claim 1, the implementing further comprising storing the point-in-time query within a query repository.

7. The non-transitory computer-readable medium of claim 6, the implementing further comprising:
modifying at least one of a point-in-time query type associated with the stored point-in-time query, or a date associated with the stored point-in-time query;
compiling the modified point-in-time query; and
executing the compiled modified point-in-time query.

8. The non-transitory computer-readable medium of claim 1, the implementing further comprising storing the case series in a case series repository.

9. The non-transitory computer-readable medium of claim 1, wherein the case series comprises one or more adverse event cases, and wherein each adverse event case comprises a data record that represents an adverse event.

10. The non-transitory computer-readable medium of claim 1, wherein the case series comprises one or more reports or patient identifiers that are related to the safety of one or more drugs.

11. A computer-implemented method for implementing a point-in-time query, the computer-implemented method comprising:
receiving a selection of a point-in-time query type, from one or more point-in-time query types, from a user;
retrieving metadata, from a repository, that comprises structured query language information based on the selected point-in-time query type;
creating a point-in-time query for a drug safety database based on the retrieved metadata and a date, the drug safety database including a plurality of adverse event records, each adverse event record including an effective end date indicating when a subsequent revision of the adverse event record was stored in the drug safety database, a patient identifier and drug safety data associated with a patient, the point-in-time query including a comparison of the date with the adverse event record effective end date;
compiling the point-in-time query to create a compiled point-in-time query; and
executing the compiled point-in-time query on the drug safety database to create a case series.

12. The computer-implemented method of claim 11, further comprising:
receiving a selection of the date from the user,
wherein each adverse event record includes an effective start date indicating when the adverse event record was stored in the drug safety database, and
wherein the point-in-time query further includes a comparison of the date with the adverse event record effective start date.

13. The computer-implemented method of claim 11, further comprising:
creating a user-defined point-in-time query type;
creating metadata, associated with the user-defined point-in-time query type, including structured query language information; and
storing the created metadata in the repository.

14. The computer-implemented method of claim 11, further comprising storing the point-in-time query within a query repository.

15. The computer-implemented method of claim 14, further comprising:
modifying at least one of a point-in-time query type associated with the stored point-in-time query, or a date associated with the stored point-in-time query;
compiling the modified point-in-time query; and
executing the compiled modified point-in-time query.

16. A system for implementing a point-in-time query, the system comprising:
a processor;
a memory configured to store one or more instructions;
a point-in-time query type selection module configured to receive a selection of a point-in-time query type, from one or more point-in-time query types, from a user;
a metadata retrieval module configured to retrieve metadata, from a repository, that comprises structured query language information based on the selected point-in-time query type;
a point-in-time query creation module configured to create a point-in-time query for a drug safety database based on the retrieved metadata and a date, the drug safety database including a plurality of adverse event records, each adverse event record including an effective end date indicating when a subsequent revision of the adverse event record was stored in the drug safety database, a patient identifier and drug safety data associated with a patient, the point-in-time query including a comparison of the date with the adverse event record effective end date;
a point-in-time query compilation module configured to compile the point-in-time query to create a compiled point-in-time query; and
a point-in-time query execution module configured to execute the compiled point-in-time query on the drug safety database to create a case series.

17. The system of claim 16, further comprising:
a date/time selection module configured to receive a selection of the date from the user,
wherein each adverse event record includes an effective start date indicating when the adverse event record was stored in the drug safety database, and
wherein the point-in-time query further includes a comparison of the date with the adverse event record effective start date.

18. The system of claim 16, further comprising:
a point-in-time query type creation module configured to create a user-defined point-in-time query type;
a metadata creation module configured to create metadata, associated with the user-defined point-in-time query type, including structured query language information; and
a metadata storage module configured to store the created metadata in the repository.

19. The system of claim 16, further comprising a point-in-time query storage module configured to store the point-in-time query within a query repository.

20. The system of claim 19, further comprising:
a point-in-time query modification module configured to modify at least one of a point-in-time query type associated with the stored point-in-time query, or a date associated with the stored point-in-time query,
wherein the point-in-time query compilation module is further configured to compile the modified point-in-time query, and
wherein the point-in-time query execution module is further configured to execute the compiled modified point-in-time query.

* * * * *

UNITED STATES PATENT AND TRADEMARK OFFICE
CERTIFICATE OF CORRECTION

PATENT NO. : 9,147,040 B2
APPLICATION NO. : 13/923483
DATED : September 29, 2015
INVENTOR(S) : Aggarwal et al.

It is certified that error appears in the above-identified patent and that said Letters Patent is hereby corrected as shown below:

On the title page 2, item [56], column 1, line 7, delete "Analylics" and insert -- Analytics --, therefor.

In the specification

Column 13, line 53, after "API" delete "that that" and insert -- that --, therefor.

Signed and Sealed this
Seventh Day of June, 2016

Michelle K. Lee
*Director of the United States Patent and Trademark Office*